United States Patent [19] [11] 4,077,982
Young et al. [45] Mar. 7, 1978

[54] 5-BENZYLOXY-1,3-DIOXANES
[75] Inventors: Sanford Tyler Young, Lockport, N.Y.; Kenneth Lee Hill, Doylestown, Pa.
[73] Assignee: FMC Corporation, Philadelphia, Pa.
[21] Appl. No.: 294,449
[22] Filed: Oct. 2, 1972

Related U.S. Application Data
[63] Continuation-in-part of Ser. No. 699,204, Jan. 19, 1968, abandoned, Ser. No. 868,278, Oct. 9, 1969, abandoned, Ser. No. 182,400, Sep. 21, 1971, abandoned, and Ser. No. 224,909, Feb. 9, 1972, Pat. No. 3,753,678.
[51] Int. Cl.² .......................................... C07D 319/06
[52] U.S. Cl. ............................. 260/340.7; 260/329 R; 260/329 F; 260/297 R; 71/88
[58] Field of Search ............ 260/340.7, 329 F, 329 R, 260/297 R

[56] References Cited
U.S. PATENT DOCUMENTS
2,307,894  1/1943  Mikeska ............................ 260/340.7

OTHER PUBLICATIONS
N. Baggett et al., Chemical Abstracts, vol. 55, p. 2439e, (1961).

Primary Examiner—Donald G. Daus
Assistant Examiner—Jose Tovar
Attorney, Agent, or Firm—Abner Sheffer; Harrison H. Young; H. Robinson Ertelt

[57] ABSTRACT

Herbicidal compositions containing compounds of the formula

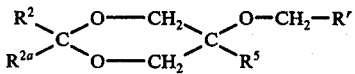

where $R^2$ is hydrogen, hydrocarbyl or substituted hydrocarbyl radical; $R^{2a}$ is hydrogen or methyl and $R^2$ and $R^{2a}$ may together form a ring; $R^5$ is hydrogen, alkyl, haloalkyl or cyanoalkyl; $R^r$ is aryl, substituted aryl or heterocyclyl.

5 Claims, No Drawings

5-BENZYLOXY-1,3-DIOXANES

This application is a continuation-in-part of Ser. No. 699,204 filed Jan. 19, 1968 now abandoned, Ser. No. 868,278 filed Oct. 9, 1969, now abandoned, and Ser. No. 182,400 filed Sept. 21, 1971, now abandoned, and Ser. No. 224,909 filed Feb. 9, 1972 now U.S. Pat. No. 3,753,678, of Aug. 21, 1973; the entire disclosures of those applications are incorporated herein by reference.

This invention relates to herbicidal compositions.

It has been found that there is unexpected herbicidal activity in the compounds of the formula

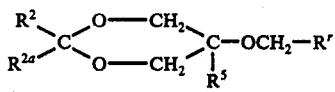

in which there is a cis relationship between the —OCH$_2$— R$'$ group and any R$^2$ group other than hydrogen;

R$^2$ is hydrogen or an alkyl, haloalkyl, cyanoalkyl, aryl, arylalkyl, aryloxyalkyl, cycloalkyl, arylalkoxyalkyl, alkoxyalkyl, alkenyl (including substituted alkenyl), alkynyl, alkylthioalkyl, alkylsulfinyalkyl or alkylsulfonylalkyl where any aryl radical is phenyl, furyl or thienyl which is unsubstituted or carries a single "X" substituent defined below:

R$^{2a}$ is hydrogen; R$^5$ is hydrogen, alkyl or haloalkyl such as chloroalkyl or bromoalkyl or cyanoalkyl;

R$'$ is a monovalent aromatic phenyl, furyl, thienyl or 2-pyridyl radical which is unsubstituted or has one, two or three, preferably less than three, "Y" substituents, as defined below:

"X", mentioned above, may be H, F, Cl, Br, lower alkyl, trifluoromethyl, lower alkoxy or benzyloxy;

"Y", mentioned above, may be H, F, Cl, Br, CN, CF$_3$, lower alkyl or lower alkoxy.

It is also found that there is herbicidal activity in compounds of the above formula in which R$^2$ and R$^{2a}$ together constitute a single divalent radical having its valences on two different carbon atoms of said radical so as to form (with the 2-carbon atom of the illustrated dioxane ring) a ring. It will be seen that such compounds have a spiro structure, i.e.

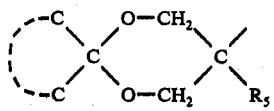

with the dotted lines indicating the remaining atoms of said divalent radical. In such spiro compounds, it is believed that the cis and trans forms are in resonant equilibrium.

Also, it is found that there is herbicidal activity in compounds of the above formula in which R$^{2a}$ is alkyl and preferably less bulky than R$^2$, (e.g. R$^2$ may be aryl or isopropyl when R$^{2a}$ is methyl) and there is a cis-relationship between R$^2$ and the —O—CH$_2$—R$'$ group.

The alkyl radicals are preferably lower alkyl and may, for example, be methyl, ethyl, propyl, isopropyl, n-butyl, isobutyl, sec-butyl or t-butyl radicals; thus the alkoxy, preferably lower alkoxy, radicals may, for example, be methoxy, ethoxy, propoxy, isopropoxy, butoxy, isobutoxy, sec-butoxy or tert-butoxy radicals. Any alkenyl or alkynyl radicals preferably have less than 6 carbon atoms. Preferably each of the substituents R$^2$, R$^5$ and R$'$ has a molecular weight below 125 when it is aliphatic and a molecular weight below 190 when it contains a ring.

Known classical steps may be employed to make the cis-5-arylmethoxy-2-substituted-1,3-dioxane compounds used in this invention. They may be made from the corresponding cis-5-hydroxy-1,3-dioxane (e.g. cis-5-hydroxy-2-phenyl-1,3-dioxane) by etherification with the appropriate compound, e.g. a compound of the formula

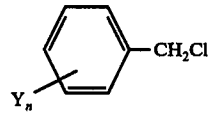

in xylene or other appropriate solvent. For example, the 5-hydroxy-dioxane in solution may be treated with sodium hydride to form the corresponding sodium alcoholate and the chloride may be added gradually thereto. The 5-hydroxy-dioxane, which is a cyclic acetal, may be produced by reaction of glycerol and an aldehyde. Such reactions usually also produce, as by-products, 4-hydroxymethyl-2-aryl-1,3-dioxolanes.

The compounds in which R$^2$ is hydrogen may be made by etherifying, with an arylmethyl chloride (or bromide) the sodium alcoholate of the 5-hydroxy-1,3-dioxane resulting from the acetalization of glycerol and formaldehyde. They may also be made by the acetalization reaction of formaldehyde and a 2-arylmethoxy-1,3-propanediol. The latter may be prepared by known methods, such as by the acid hydrolysis of the corresponding 5-arylmethoxy-2-aryl-1,3-dioxane; see West and Ludwig, J. Am. Chem. Soc. 74, 4466 (1952).

Alternatively, the dioxanes of this invention may be produced by acetalization reaction of an aldehyde or ketone with the appropriate 2-arylmethoxy-1,3-propanediol. This process is particularly advantageous when R$^2$ is a group e.g. chloromethyl, susceptible to attack by the alkaline reagent normally employed in the etherification reaction mentioned above.

Particularly advantageous for preparation of those compounds in which R$^5$ is other tha hydrogen is the process based upon 5-alkylidene-1,3-dioxanes. The appropriately substituted 5-alkylidene-1,3-dioxane is epoxidized, the epoxy compound hydrogenated to give the corresponding 5-hydroxy-5-alkyl-1,3-dioxane and that 5-hydroxy compound etherified as described above.

Preparation of the 5-cyanoalkyl compounds may be readily accomplished by reaction of the appropriate 5-haloalkyl compound with sodium cyanide.

In the herbicidal use of the material, the active cis compound may be used in admixture with the trans isomer, and such mixture may even contain a major proportion of the latter. Generally it is most economical to use materials of high cis content made by synthesis which reduce, or avoid, the formation of the trans isomer. The higher the cis content the greater is the herbicidal effect of the given mixture of cis, trans isomers. In the most preferred forms of the invention the cis compound is present in amount at least equal to that of the corresponding trans compound, e.g. the cis:trans ratio is over 3:2, more preferably over 2:1 and still more preferably at least 3:1. The aforementioned dioxolanes may also be present in the mixture as impurities.

When the 5-hydroxy-dioxanes used as the starting materials are rich in the cis forms, the resulting products have a high content of the herbicidally active cis-5-aryl-methoxy-2-aryl-1,3-dioxanes. It is also often found that on crystallization of the products (as from reaction mixtures containing a solvent such as xylene) followed by recrystallization (as from benzene-ligroin or benzene-petroleum ether mixtures) the solid products are richer in the active cis compounds, the trans compounds and dioxolanes being preferentially dissolved.

This invention provides a new class of herbicidal materials, having both pre-emergent and post-emergent activity. The materials are highly suitable for the control and elimination of grassy plants, particularly annual grasses, in the presence of broad-leaved crops, such as cotton, sugar beets, peanuts, soya beans, snap beans, lima beans, tomatoes or nursery stock. Among the compounds found to be especially effective are cis-5-(2-fluorobenzyloxy)-2-phenyl-1,3-dioxane; cis-5-(2-methylbenzyloxy)-2-phenyl-1,3-dioxane; cis-5-benzyloxy-2-(3-chlorophenyl)-1,3-dioxane; cis-5-benzyloxy-1,3-dioxane; cis-5-benzyloxy-2-(2-fluorophenyl)-1,3-dioxane; cis-5-(4-methylbenzyloxy)-2-phenyl-1,3-dioxane; cis-5-(2-bromobenzyloxy)-2-phenyl-1,3-dioxane; cis-5-(4-fluorobenzyloxy-2-phenyl-1,3-dioxane; cis-5-(3-fluorobenzyloxy)-2-phenyl-1,3-dioxane; cis-5-(2-chlorobenzyloxy)-2-phenyl-1,3-dioxane; cis-5-benzyloxy-2-(3-fluorophenyl)-1,3-dioxane; cis-5-(2-fluorobenzyloxy)2-(3-fluorophenyl)-1,3-dioxane; cis-5-benzyloxy-2-(3-methylphenyl)-1,3-dioxane; cis-5-(2-fluorobenzyloxy)-2-(3-chlorophenyl)-1,3-dioxane; cis-5-benzyloxy-2-(3-benzyloxyphenyl)-1,3-dioxane; cis-5-benzyloxy-2-(3-methoxyphenyl)-1,3-dioxane; cis-5-(2-methylbenzyloxy)-2-(3-chlorophenyl)-1,3-dioxane; 2-c-ethyl-5-r-(2-fluorobenzyloxy)-5-methy-1,3-dioxane; 2-c-ethyl-5-methyl-5-r-(2-methylbenzyloxy)-1,3-dioxane; 5-r-(2-chlorobenzyloxy)-2-c-ethyl-5-methyl-1,3-dioxane; 2-c-chloromethyl-5-r-(2-fluorobenzyloxy)-5-methyl-1,3-dioxane;

For compounds having an X or Y substituent other than H, outstanding herbicidal activity, particularly for preemergence application, has been observed especially in compounds having that Y substituent at the 2-position (ortho position) of the ring to which it is attached (e.g., 2-chloro-, 2-fluoro-, 2-bromo-, or 2-methylbenzyloxy compounds) and also in compounds in which X is at the 3-position (meta-position) of the other ring (e.g., where $R^2$ is 3-chlorophenyl, 3-methylphenyl, 3-fluorophenyl, 3-methoxyphenyl and 3-benzyloxyphenyl). Compounds having fluoro groups, as in the compounds of Examples 9 and 13, show outstanding post-emergence as well as preemergence activity.

Particularly preferred are those compounds in which $R^2$ is ethyl or chloromethyl.

The stereochemistry of the derivatives of 5-hydroxy-1,3-dioxane has been discussed in the scientific literature [see, for example, Baggett et al., J. Chem. Soc., 2574 (1960) and Dobinson and Foster, J. Chem. Soc. 2338 (1961)]. As pointed out in the literature, a cis-relationship between the 5-substituent and the 2-substituent occurs when the 5-substituent is in an axial position and the 2-substituent is in an equatorial position. Much information concerning the structures involved can be obtained from nuclear magnetic resonance spectra. The drawings accompanying application Ser. No. 224,909 show nuclear magnetic resonance (nmr) spectra of the following compounds or mixtures:

FIG. 1, cis-5-benzyloxy-2-phenyl-1,3-dioxane;
FIG. 2, trans-5-benzyloxy-2-phenyl-1,3-dioxane;
FIG. 3, 4-benzyloxymethyl-2-phenyl-1,3-dioxolane;
FIG. 4, a mixture of the compounds of FIGS. 1, 2, and 3;
FIG. 5, 5-(2-fluorobenzyloxy)-2-phenyl-1,3-dioxane rich in the cis form thereof;
FIG. 6, cis-5(2-methylbenzyloxy)-2-phenyl-1,3-dioxane;
FIG. 7, c-5-benzyloxy-5-methyl-2-phenyl-1,3-dioxane;
FIG. 8, t-5-benzyloxy-5-methyl-2-phenyl-1,3-dioxane;
FIG. 9, r-5-ethyl-c-5-(2-fluorobenzyloxy)-5-methyl-1,3-dioxane;
FIG. 10, r-5-ethyl-t-5-(2-fluorobenzyloxy)-5-methyl-1,3-dioxane;
FIG. 11, c-5-(2-fluorobenzyloxy)-5-methyl-r-2-phenyl-1,3-dioxane;
FIG. 12, t-5-(2-fluorobenzyloxy)-5-methyl-r-2-phenyl-1,3-dioxane;
FIG. 13, c-5-(benzyloxy)-r-2-isopropyl-5-methyl-1,3-dioxane;
FIG. 14, 5-benzyloxy-2-(2-furyl)-1,3-dioxane (30%cis).

All spectra were run on a Varian A-60A nmr at 60 mc using $CDCl_3$ as solvent under normal operating conditions with the sample temperature ca 37°. In accordance with accepted practice, tetramethylsilane was used as an internal standard in making the measurements.

The cis and trans- characterizations used herein and the estimated relative amounts of these species are based on nmr (nuclear magnetic resonance) and VPC (vapor phase chromatography) measurements. As seen in FIG. 1 the nmr spectrum of cis-5-benzyloxy-2-phenyl-1,3-dioxane shows a multiplet (a "jagged peak") at about 3.22 ppm with a base width of about 10 cps (indicating the presence of an equatorial proton on the 5-carbon) and also a characteristic peak at about 5.47 ppm. The corresponding trans compound (FIG. 2) does not show the same multiplet at about 3.22 ppm but shows a characteristic peak at about 5.37 ppm. The mixture of stereoisomers of the corresponding dioxolane (FIG. 3) shows two peaks at 5.73 and 5.89 ppm. The mixture of all these compounds (FIG. 4) shows the multiplet at 3.22 ppm, but this has a much smaller amplitude than that of the one seen in FIG. 1 owing to the smaller proportion (about one fourth of the mixture) of the cis-dioxane compound. FIG. 4 also shows the four peaks between 5.25 and 5.95 ppm previously discussed; the relative proportions of the individual isomers can be determined by comparing the individual areas under these peaks, in known manner.

In FIG. 5, (for a compound similar to that of FIG. 1, but carrying a 2-fluoro substituent on the benzyloxy group), there is a peak at about 3.34 ppm. having a base width of about 10 cps. There is also a characteristic peak at 5.54 ppm. In FIG. 6, (for a similar compound having a 2-methyl substituent) there is also a multiplet at 3.32 ppm. having a base width of about 10 cps and a peak at 5.55 ppm.

In FIG. 5, a comparison of the total area under the peaks from about 3.84 ppm. to 4.50 ppm. (contributed mainly by the protons at the 4- and 6-carbon atoms) with the other information supplied by this nmr spectrum, indicates the presence of 5-hydroxy-2-phenyl-1,3-dioxane in proportion of about 12%.

It has been found that the cis and trans components can be identified by vapor phase chromatography (VPC). In operating with a certain chromatographic column it was found that the dioxolanes were eluted first, followed by the trans-5-arylmethoxy-2-aryl-1,3-dioxane, and lastly, the corresponding cis-dioxane compound. The column used was a 5 foot column, one-four inch in diameter, containing 10% "Carbowax 20M TPA" [terephthalic acid - terminated polyethylene oxide] on granules of "Chromosorb W" (a diatomaceous earth). The instrument used a thermal conductivity detector with helium as the carrier gas. The operating temperature of the column was 240° C and the operating gas flow was 300 cc/min. In the analysis, about 20 microliters of a 10% solution of the test sample in benzene was injected onto the column in well-known manner. The relative amounts of the individual materials emerging from the column can be readily determined in conventional manner and these components can be identified as cis or trans, based on their order of emergence as described above. Incidentally, this order of emergence differs from that observed for the corresponding 5-hydroxy-2-phenyl-1,3-dioxane; in the latter case the cis compound emerges before the trans isomers.

FIGS. 7-14 show the nmr spectra of the compounds named thereon. The legends indicate the significance of the various features of the spectra; the same letter is used for corresponding protons in each spectrum so that the figures may be correlated. In accordance with conventional practice there are lines for integrations of the various peaks and the integrations are done twice, so that there are pairs of integration lines. As is conventional, the spectra show an extension of the left hand end of the spectrum, displaced upward and to the right so that the whole spectrum can appear in the available space; in the spectra no significant features are apparent in the range represented by that line. The integrations indicate the areas under the peaks; thus in FIG. 7, the area under peak A is equivalent to 3 protons and in FIG. 8, the area under the broader but lower peak A is also equivalent to 3 protons.

Among the various features evident from a comparison of FIGS. 7 and 8, the following differences may be noted. Where there is a cis-relationship (FIG. 7), the peak F is at a lower field (i.e. higher ppm ($\delta$)) and the peak G is also usually at a lower field than is the case where there is a trans-relationship (FIG. 8); these features are also evident in FIGS. 1 and 2. Also for the 5-methyl compounds, where there is a cis-relationship, peak A is at a higher field and the group of peaks B, C, D, E covers a larger range of ppm than is the case where there is a trans-relationship.

The preparation, properties, and herbicidal activity of representative compounds of this invention are illustrated further in the following examples, in which all temperatures are in degrees Centigrade. Additionally, when reference is made to a reduced pressure without specifying that pressure, it is to be assumed that the reduced pressure is that attainable by means of a water aspirator.

EXAMPLE 1

In this Example there was used a white crystalline sample of 5-benzyloxy-2-phenyl-1,3-dioxane of melting point 75°-76° C. and of high cis content.

The pre- and post-emergence herbicidal activity of this material was tested in the following manner: lima beans, corn, lettuce, mustard and crabgrass were planted in rows side-by-side in shallow flat-bed trays filled with a mixture of equal amounts of silt-loam and sandy-loam soils. The material to be tested was dissolved in an acetone-water mixture and was sprayed on a soil at a rate of 8 pounds per acre for pre-emergence screening. In post-emergence screening, plants were sprayed with the acetone-water solution at a rate of 8 lbs/acre approximately two weeks after planting, i.e. when corn plants have developed 3 to 4 true leaves. Two weeks after application, the phytotoxicity of the material was evaluated for both pre- and post-emergence tests. Untreated plants were maintained for comparison in both procedures. There was essentially complete kill of corn and crabgrass in both pre- and post-emergence screenings while none of the other plants were killed.

EXAMPLE 2

In this Example there was used a cis-5-benzyloxy-2-phenyl-1,3-dioxane sample prepared in the following manner:

To a solution of 16.8 g cis-5-hydroxy-2-phenyl-1,3-dioxane in 150 ml xylene was added in small portions 4.0 g of a 60 percent suspension of sodium hydride in mineral oil. The mixture was then maintained at 40° C. for 1 hour. To this solution was added dropwise 13.9 g benzyl chloride. The reaction mixture was then maintained at 110° C. for 6 hours. After the reaction mixture had been cooled, it was filtered and evaporated under reduced pressure. The resulting solid was recrystallized from a benzene-ligroin mixture. The melting point of the recrystallized product was 73°-75° C. VPC and nmr studies revealed the product to be 80-90 percent cis-5-benzyloxy-2-phenyl-1,3-dioxane. The product showed excellent selective pre- and post-emergence herbicidal activity, as shown in the following tabulations in which the numbers represent percent kill at the indicated dosages.

| Test Plant Species | Pre-emergence Evaluation at the dosage (in pounds per acre) indicated below | | | |
|---|---|---|---|---|
| | 0.75 | 1.5 | 3.0 | 6.0 |
| Peanuts | 0 | 0 | 0 | 0 |
| Rice | 100 | 100 | 100 | 100 |
| Alsike clover | 0 | 0 | 0 | — |
| Cotton | 0 | 0 | 0 | 0 |
| Tomato | 0 | 0 | 0 | 0 |
| Wheat | 10 | 10 | 90 | 80 |
| Corn | 80 | 80 | 100 | 100 |
| Meadow fescue | 100 | 100 | 100 | 100 |
| Sugar beet | 0 | 0 | 0 | 0 |
| Dallisgrass | 100 | 100 | 100 | 100 |
| Crabgrass | 100 | 100 | 100 | 100 |
| Cucumber | 0 | 0 | 0 | 10 |
| German hay millet | 100 | 100 | 100 | 100 |
| Flax | 70 | 80 | 90 | 95 |
| Lambsquarter | 0 | 0 | 0 | 0 |
| Wild oats | 75 | 60 | 90 | 100 |
| Giant foxtail | 100 | 100 | 100 | 100 |
| Cabbage | 0 | 0 | 0 | 0 |
| Peppers | 0 | 0 | 0 | 0 |
| Lettuce | 0 | 0 | 0 | 0 |
| Lima beans | 0 | 0 | 0 | 0 |
| Barnyard grass | 0 | 0 | 20 | 40 |
| Pigweed | 0 | 0 | 0 | 0 |
| Rye grass | 75 | 25 | 80 | 95 |
| Carrots | 0 | 0 | 0 | 0 |
| Alfalfa | 0 | 0 | 0 | 0 |

| Post-emergence Evaluation at a dosage of 6 lbs./acre | |
|---|---|
| Test Plant Species | |
| Peanuts | 0 |
| Rice | 90 |
| Alsike clover | 30 |
| Cotton | 0 |

-continued

| Post-emergence Evaluation at a dosage of 6 lbs./acre | |
|---|---|
| Test Plant Species | |
| Tomato | 0 |
| Wheat | 0 |
| Corn | 100 |
| Meadow fescue | 25 |
| Dallisgrass | 95 |
| Crabgrass | 100 |
| Cucumber | 0 |
| German hay millet | 100 |
| Flax | 100 |
| Lambsquarter | 100 |
| Wild oats | 90 |
| Giant foxtail | 100 |
| Lettuce | 0 |
| Lima beans | 0 |
| Barnyard grass | 100 |
| Rye grass | 100 |
| Carrots | 20 |
| Alfalfa | 0 |

EXAMPLE 3

This Example illustrates a typical preparation of a 5-arylmethoxy-2-aryl-1,3-dioxane from the corresponding 5-hydroxy compound and arylmethyl chloride. The particular product made in this Example was cis-5-(3,4-dichlorobenzyloxy)-2-phenyl-1,3-dioxane.

Sodium hydride (4.0 g, 0.101 mol) was added to cis-5-hydroxy-2-phenyl-1,3-dioxane (16.8 g, 0.1 mol) in 150 ml of xylene. The slurry was stirred at 40°–50° C for ½ hour and 3,4-dichlorobenzyl chloride (19.6 g, 0.1 mol) was added. The slurry was refluxed for 6 hours and then cooled and washed with 5% sodium bicarbonate (2 × 50 ml) and water (2 × 100 ml). The solvent was stripped from the dried organic layer under reduced pressure to give 29.8 g of solid, m.p. 72°–78° C. Two recrystallizations from benzene-ligroin gave cis-5-(3,4-dichlorobenzyloxy)-2-phenyl-1,3-dioxane, m.p. 77°–78° C. VPC analyses indicated that it was nearly pure cis isomer.

EXAMPLE 4

Other herbicidally active products which may be prepared in the same way (using the arylmethyl chloride or in certain cases the corresponding arylmethyl bromide and the corresponding 5-hydroxy-2-aryl-1,3-dioxane) include the following:

cis-5-(4-methylbenzyloxy)-2-phenyl-1,3-dioxane (m.p. 112.5°–113° C; VPC analysis indicated nearly pure cis);

cis-5-(2-chlorobenzyloxy)-2-phenyl-1,3-dioxane (m.p. 95°–96.5° C; VPC analysis indicated 85% cis);

cis-5-(4-chlorobenzyloxy)-2-phenyl-1,3-dioxane (m.p. 110°–111° C; VPC analysis indicated 87% cis);

cis-5-(2,4-dichlorobenzyloxy)-2-phenyl-1,3-dioxane (m.p. 116°–117° C; VPC analysis indicated nearly pure cis);

5-(3-methylbenzyloxy)-2-phenyl-1,3-dioxane (m.p. 65°–66.5° C; VPC analysis indicated 51% cis);

cis-5-(2,6-dichlorobenzyloxy)-2-phenyl-1,3-dioxane (m.p. 90°–92° C; VPC analysis indicated 75% cis);

cis-5-(3-chlorobenzyloxy)-2-phenyl-1,3-dioxane (m.p. 57°–58° C; VPC analysis indicated 87% cis);

cis-5-(3,4-dimethylbenzyloxy)-2-phenyl-1,3-dioxane (m.p. 88°–90° C; VPC analysis indicated 82% cis);

cis-5-(2-methylbenzyloxy)-2-phenyl-1,3-dioxane (m.p. 79°–80° C; VPC analysis indicated nearly pure cis);

cis-5-(2-fluorobenzyloxy)-2-phenyl-1,3-dioxane (m.p. 70°–71° C; VPC analysis indicated 90% cis);

cis-5-(3-fluorobenzyloxy)-2-phenyl-1,3-dioxane (m.p. 64°–65° C; VPC analysis indicated 79% cis);

cis-5-(4-fluorobenzyloxy)-2-phenyl-1,3-dioxane (m.p. 57°–59° C; VPC analysis indicated 69% cis, and 2% trans);

cis-5-(2,5-dichlorobenzyloxy)-2-phenyl-1,3-dioxane (m.p. 76°–77° C; VPC analysis indicated nearly pure cis);

5-(2,3,6-trichlorobenzyloxy)-2-phenyl-1,3-dioxane (here an oil product was obtained, from which a fraction was distilled at 210°–213° C. at $10^{-5}$ mm; this crystallized on cooling, giving a material of m.p. 113°–114° C. which VPC analysis indicated contained 34–39% cis and 61–66% trans);

cis-5-(2,4-dimethylbenzyloxy)-2-phenyl-1,3-dioxane (m.p. 93.5°–94° C; VPC analysis indicated nearly pure cis);

cis-5-(2,5-dimethylbenzyloxy)-2-phenyl-1,3-dioxane (m.p. 102°–103° C; VPC analysis indicated nearly pure cis);

cis-5-benzyloxy-2-(2-chlorophenyl)-1,3-dioxane (m.p. 100°–100.5° C; VPC analysis indicated nearly pure cis);

cis-5-benzyloxy-2-(4-chlorophenyl)-1,3-dioxane (m.p. 125°–126° C; VPC analysis indicated 95% cis);

cis-5-benzyloxy-2-(3-chlorophenyl)-1,3-dioxane (m.p. 85°–85.5° C; VPC analysis indicated 97% cis);

cis-5-(3-trifluoromethylbenzyloxy)-2-phenyl-1,3-dioxane (m.p. 43°–45° C; VPC analysis indicated 84% cis, 9% trans);

cis-5-(2-cyanobenzyloxy)-2-phenyl-1,3-dioxane (m.p. 115°–116° C; VPC analysis indicated nearly pure cis);

cis-5-(2-bromobenzyloxy)-2-phenyl-1,3-dioxane (m.p. 93°–94° C; VPC analysis indicated 85% cis, 11% trans);

5-(4-cyanobenzyloxy)-2-phenyl-1,3-dioxane (m.p. 112°–113° C; VPC analysis indicated 66% cis, 33% trans);

cis-5-(2-methoxybenzyloxy)-2-phenyl-1,3-dioxane (b.p. 180°–190° C at $10^{-5}$ mm; VPC analysis indicated 72% cis);

cis-5-benzyloxy-2-(2-bromophenyl)-1,3-dioxane (b.p. 210°–215° C at $10^{-5}$ mm; VPC analysis indicated nearly pure cis);

5-benzyloxy-2-(2-ethoxyphenyl)-1,3-dioxane (b.p. 180°–185° C at $10^{-5}$ mm; VPC analysis indicated that it contained 11% cis, 27% trans, and 62% of the isomeric dioxolane);

5-benzyloxy-2-(2-methoxyphenyl)-1,3-dioxane (b.p. 190°–195° C at $10^{-5}$ mm; VPC analysis indicated that it contained 14% cis, 31% trans, and 55% of the isomeric dioxolane);

5-benzyloxy-2-(2-fluorophenyl)-1,3-dioxane (b.p. 165°–170° C at $10^{-5}$ mm; VPC analysis indicated 43%, cis);

cis-5-benzyloxy-2-(3-bromophenyl)-1,3-dioxane (m.p. 92°–93° C; VPC analysis indicated nearly pure cis);

cis-5-benzyloxy-2-(3,5-dichlorophenyl)-1,3-dioxane (m.p. 97°–98° C.; VPC analysis indicated nearly pure cis);

cis-5-[2-(trifluoromethyl)benzyloxy)]-2-phenyl-1,3-dioxane (m.p. 68°–69° C.; VPC analysis indicated nearly pure cis);

cis-5-[(3-trifluoromethyl)benzyloxy]-2-phenyl-1,3-dioxane (m.p. 43°–45° C; VPC analysis indicated 84% cis);
cis-5-(3-bromobenzyloxy)-2-phenyl-1,3-dioxane;
cis-5-(2-chlorobenzyloxy)-2-(3-chlorophenyl)-1,3-dioxane;
cis-5-(2-fluorobenzyloxy)-2-(3-chlorophenyl)-1,3-dioxane;
cis-5-(2-bromobenzyloxy)-2-(3-chlorophenyl)1,3-dioxane;
cis-5-(2-methylbenzyloxy)-2-(3-chlorophenyl)-1,3-dioxane;
cis-5-(2-trifluoromethylbenzyloxy)-2-(3f -chlorophenyl)-1,3-dioxane;
cis-5-(2-chlorobenzyloxy)-2-(2-fluorophenyl)-1,3-dioxane;
cis-5-(2-fluorobenzyloxy)-2-(2-fluorophenyl)-1,3-dioxane;
cis-5-(3-fluorobenzyloxy)-2-(2-fluorophenyl)-1,3-dioxane;
cis-5-(4-methylbenzyloxy)-2-(2-fluorophenyl)-1,3-dioxane;
cis-5-(2-chlorobenzyloxy)-2-(3-fluorophenyl)-1,3-dioxane;
cis-5-(2-fluorobenzyloxy)-2-(3-fluorophenyl)-1,3-dioxane;
cis-5-(3-fluorobenzyloxy)-2-(3-fluorophenyl)-1,3-dioxane;
cis-5-(2-bromobenzyloxy)-2-(3-fluorophenyl)-1,3-dioxane;
cis-5-(2-methylbenzyloxy)-2-(3-fluorophenyl)-1,3-dioxane;
cis-5-(4-methylbenzyloxy)-2-(3-fluorophenyl)-1,3-dioxane;
cis-5-benzyloxy-2-(3-cyanophenyl)-1,3-dioxane;
cis-5-(2-fluorobenzyloxy)-2-(3-cyanophenyl)-1,3-dioxane;
cis-5-(2-fluorobenzyloxy)-2-(3-bromophenyl)-1,3-dioxane;
cis-5-benzyloxy-2-(3-methylphenyl)-1,3-dioxane;
cis-5-(2-fluorobenzyloxy)-2-(3-methylphenyl)-1,3-dioxane;
cis-5-(2-methylbenzyloxy)-2-(3-methylphenyl)-1,3-dioxane;
cis-5-benzyloxy-2-(3-methoxyphenyl)-1,3-dioxane;
cis-5-(2-fluorobenzyloxy)-2-(3-methoxyphenyl)-1,3-dioxane;
cis-5-(2-methylbenzyloxy)-2-(3-methoxyphenyl)-1,3-dioxane;
cis-5-(3-fluorobenzyloxy)-2-phenyl-1,3-dioxane.

EXAMPLE 5

This Example illustrates the preparation of intermediates useful in the manufacture of compounds listed in Example 4.

(5a) 2,5-dichlorobenzyl bromide:

A solution of 8.0 g 2,5-dichlorotoluene and 0.5 g benzoyl peroxide in 75 ml carbon tetrachloride was heated to reflux temperature. To this was added portionwise 9.0 g N-bromosuccinimide. The resulting solution was refluxed for 5 hours. The mixture was cooled to room temperature, filtered and washed successively with two 50 ml volumes of 5 percent aqueous sodium bicarbonate, two 50 ml volumes of 5 percent aqueous sodium sulfite and two 50 ml volumes of water. The mixture was dried over magnesium sulfate, filtered, and evaporated under reduced pressure to a yellow oil. The oil was distilled and that fraction distilling at 75°–78° C/0.5mm (2,5-dichlorobenzyl bromide) crystallized upon cooling, m.p. 39°–40° C.

(5b) 2,3,6-trichlorobenzyl bromide (b.p. 132°–134° C at 4 mm) was made by the foregoing method, substituting 2,3,6-trichlorotoluene for the 2,5-dichlorotoluene.

(5c) 5-hydroxy-2-(2-chlorophenyl)-1,3-dioxane:

A mixture of 140 g 2-chlorobenzaldehyde, 92 g glycerol and 4 ml 40 percent sulfuric acid was heated under a carbon dioxide atmosphere at 100° C for 6 hours. After cooling the reaction mixture to room temperature, the resultant oil was dissolved in ether. The ether solution was washed with a saturated aqueous potassium carbonate solution and then dried by magnesium sulfate. The solution was then filtered and evaporated under reduced pressure. A small amount of HCl was bubbled through the resulting oil; which oil was then placed under refrigeration for several hours. Since crystallization did not occur, the oil product was dissolved in ether; the ether solution was washed with two 100 ml volumes of 1 percent ammonium hydroxide and with water, dried over magnesium sulfate, filtered, and evaporated in vacuo. The resultant oil was distilled and that fraction distilling at 117°–118° C/10$^{-5}$ mm contained 5-hydroxy-2-(2-chlorophenyl)-1,3-dioxane.

(5d) 5-hydroxy-2-(4-chlorophenyl)-1,3-dioxane:

Using the method of Example 21, 42 g 4-chlorobenzaldehyde, 27.6 g glycerol and 4 ml 40 percent sulfuric acid were reacted to form 5-hydroxy-2-(4-chlorophenyl)-1,3-dioxane. The reaction mixture was dissolved in benzene and washed successively with two 50 ml volumes of 5 percent aqueous sodium bicarbonate, two 50 ml volumes aqueous sodium bisulfite and two 100 ml volumes of water. The benzene solution was dried with magnesium sulfate, filtered and evaporated under reduced pressure to form an oil which crystallized, m.p. 95°–100° C (recrystallized from benzene-ligroin).

(5e) 2-(2-bromophenyl)-5-hydroxy-1,3-dioxane:

A solution of 25 g 2-bromobenzaldehyde, 12.4 g glycerol and 1 ml 40 percent sulfuric acid in 50 ml benzene was maintained with stirring at 80°–100° C for 24 hours. The resulting solution was washed with an aqueous potassium carbonate solution, dried with magnesium sulfate and evaporated under reduced pressure. The oil product was distilled, and that fraction distilling at 148°–150° C/10$^{-5}$ mm contained 2-(2-bromophenyl)-5-hydroxy-1,3-dioxane.

(5f) 2-(2-ethoxyphenyl)-5-hydroxy-1,3-dioxane:

Using the method of Example 5e, 30 g 2-ethoxybenzaldehyde was reacted with 18.4 g glycerol to form 2-(2-ethoxyphenyl)-5-hydroxy-1,3-dioxane, crude b.p. 140°–148° C/10$^{-5}$ mm.

(5g) 5-hydroxy-2-(2-methoxyphenyl)-1,3-dioxane:

Using the method of Example 5e, 40.8 g 2-methoxybenzaldehyde and 27.6 g glycerol were reacted to form 5-hydroxy-2-(2-methoxyphenyl)-1,3-dioxane, crude b.p. 150°–155° C/10$^{-5}$ mm.

(5h) 2-(2-fluorophenyl)-5-hydroxy-1,3-dioxane:

Using the method of Example 5g, except no solvent was necessary, 24.8 g 2-fluorobenzaldehyde and 18.4 g glycerol were reacted to form 2-(2-fluorophenyl)-5-hydroxy-1,3-dioxane. The product was cooled and dissolved in 100 ml ether. The ether solution was washed with an aqueous potassium carbonate solution, dried with magnesium sulfate, filtered and evaporated under reduced pressure. The resultant oil was distilled, and that fraction distilling at 140°–145° C/10$^{-5}$ mm contained 2-(2-fluorophenyl)-5-hydroxy-1,3-dioxane.

(5i) 2-(3-bromophenyl)-5-hydroxy-1,3-dioxane:

A mixture of 27.7 g 3-bromobenzaldehyde, 13.8 g glycerol and 2 ml 40 percent sulfuric acid was heated with stirring at 100°–110° C for 40 hours. The mixture was then cooled, 200 ml benzene was added and the mixture was heated at 80°–85° C until the theoretical amount of water produced during the reaction was collected. The benzene solution of potassium carbonate was diluted with 200 ml ether. The benzene solution was washed with three 100 ml volumes of water, dried over magnesium sulfate and evaporated. The oil product was distilled and that fraction which distilled at 131°–134° C/5 × $10^{-5}$ mm was used directly for synthesis of 5-benzyloxy-2-(3-bromophenyl)1,3-dioxane.

EXAMPLE 6

This Example illustrates the production of 5-benzyloxy-1,3-dioxane and compounds in which the benzyloxy group carries a "Y" substituent.

(a) 12.0 g (0.066 mol) of 2-benzyloxy-1,3-propanediol, 2.0 g of trioxymethylene, 0.1 g of p-toluenesulfonic acid and 100 ml of benzene were placed in a flask equipped with a stirrer, condenser and Dean-Stark moisture trap. The flask was heated to 80° C and refluxing was continued until 1.4 ml H$_2$O was collected. The mixture was then cooled to room temperature, washed twice with 100 ml portions of aqueous 2% solution of sodium bicarbonate, and then twice with 100 ml portions of water. The washed benzene layer was then dried over magnesium sulfate; the latter drying agent was then filtered off and the solvent was removed by evaporation under reduced pressure. The remaining oil was then distilled to recover a fraction (5-benzyloxy-1,3-dioxane) which distilled at a pot temperature of 72°–80° C at $10^{-5}$ mm.

(b) In another method of preparing the 5-benzyloxy-1,3-dioxane, the starting material was 5-hydroxy-1,3-dioxane (Tetrahedron 7, 10–18 (1959)). The latter was prepared by first reacting glycerol with trioxymethylene, in the presence of HCl as a catalyst to form a mixture of cyclic acetals (J. Am. Chem. Soc. 50, 3124 (1928)) which was then esterified with benzoyl chloride, in the presence of pyridine, yielding on recrystallization the benzoate 5-hydroxy-1,3-dioxane melting at 71°–72° C (J. Am. Chem. Soc. 50, 3120 (1928)). This ester was then split by reaction with sodium methylate in chloroform, to produce the purified 5-hydroxy-1,3-dioxane which was taken off as a cut boiling at 95°–96° C at 22 mm. Three grams (0.029 mol) of the latter product and 100 ml of benzene were placed in a flask equipped with a stirrer, condenser, thermometer and addition funnel. While stirring, 1.1 g of sodium hydride was added portionwise; hydrogen evolved. Next, after the resulting slurry had been kept at room temperature for ½ hour without further addition of ingredients while stirring continued, 3.65 g of benzyl chloride was added dropwise over a fifteen minute period. When all the benzyl chloride had been added the mixture was heated to 80° C and maintained at this temperature for 24 hours while stirring continued. The slurry thus obtained was then washed twice with 100 ml portions of water and the resulting organic layer was dried over MgSO$_4$. This drying agent was then filtered off and the solvent was removed under reduced pressure, yielding an oil which was then distilled under reduced pressure to give a fraction (5-benzyloxy-1,3-dioxane) boiling at 80°–82° C at 0.15 mm and having an estimated purity of about 85%.

The foregoing methods may be used in the preparation of the following herbicidal compounds: 5-(2-chlorobenzyloxy)-1,3-dioxane; 5-(2-fluorobenzyloxy)-1,3-dioxane; 5-(2-methylbenzyloxy)-1,3-dioxane; and 5-(4-methylbenzyloxy)-1,3-dioxane. In such preparations the 2-arylmethoxy-1,3-propane-diol used as a starting material can be prepared by the acid hydrolysis (J. Am. Chem. Soc. 74, 4466 (1952)) of the corresponding 5-arylmethoxy-2-phenyl-1,3-dioxane. Alternatively, 5-hydroxy-1,3-dioxane can be etherified with the substituted benzyl chloride or bromide, in which the substituent is as named above.

EXAMPLE 7 cis-5-(2,6-Dichlorobenzyloxy)-2-phenyl-1,3-dioxane

Sodium hydride (2.0 g of 61%, 0.05 mole) was added to cis-5-hydroxy-2-phenyl-1,3-dioxane (8.4 g, 0.047 mole) in 150 ml of xylene. The slurry was stirred at 40° for 1 hour and 2,6-dichlorobenzyl bromide (12.0 g, 0.05 mole) was added. The slurry was heated at 110° for 6 hours, then filtered to remove the precipitated solid. The filtrate was concentrated in vacuo to give 22.6 g of yellow oil which solidified on standing, m.p. 65°–84° C. Recrystallization from benzene-petroleum ether gave 10.8 g of white solid, m.p. 71°–73° C. Further purification gave a white solid, m.p. 90°–92° C. Analysis by VPC showed the product to be 75% cis-5-(2,6-dichlorobenzyloxy)-2-phenyl-1,3-dioxane and 25% trans-5-(2,6-dichlorobenzyloxy)-2-phenyl-1,3-dioxane.

EXAMPLE 8 cis-5-(2-Methylbenzyloxy)-2-phenyl-1,3-dioxane

Sodium hydride (2.0 g of 61%, 0.05 mole) was added to cis-5-hydroxy-2-phenyl-1,3-dioxane (8.5 g, 0.05 mole) in 150 ml of xylene. The slurry was stirred at ambient temperature for 0.5 hour and 2-methylbenzyl bromide (9.3 g, 0.05 mole) was added. The slurry was heated at 100° C for 6 hours, cooled, and washed with water (2 × 75 ml). The organic layer was separated, dried over magnesium sulfate and concentrated to give 12.4 g of product, m.p. 77°–82° C. Recrystallization from benzene-ligroin gave 5.3 g, m.p. 78°–79° C. Analysis by VPC indicated the product to be 100% cis-5-(2-methylbenzyloxy)-2-phenyl-1,3-dioxane.

EXAMPLE 9 cis-5-(2-Fluorobenzyloxy)-2-phenyl-1,3-dioxane

Using the method of Example 8, cis-5-hydroxy-2-phenyl-1,3-dioxane (8.4 g, 0.047 mole) was reacted with sodium hydride (2.0 g of 61%, 0.047 mole). The reactant sodium salt was reacted with 2-fluorobenzyl chloride (7.2 g, 0.05 mole) to give, after recrystallization from benzene-ligroin, 2.8 g of white solid, m.p. 65°–67° C, and on further recrystallization, a solid, m.p. 70°–71° C. Analysis by VPC indicated the product to be 90% cis-5-(2-fluorobenzyloxy)-2-phenyl-1,3-dioxane.

EXAMPLE 10 cis-5-(2-Bromobenzyloxy)-2-phenyl-1,3-dioxane

Sodium hydride (2.0 g of 61%, 0.05 mole) was added to 5-hydroxy-2-phenyl-1,3-dioxane (8.4 g, 0.047 mole) in 150 ml of dioxane. The slurry was stirred at ambient temperature for 0.05 hour and 2-bromobenzyl bromide (12.5 g, 0.05 mole) was added. The slurry was heated at 100° C. for 12 hours, cooled and washed with water (2 × 100 ml). The organic layer was separated, dried over magnesium sulfate and concentrated to give 66.2 g of solid, which on recrystallization from benzene-ligroin gave 8.5 g of solid, m.p. 90°–91° C. Further recrystallization gave a solid, m.p. 93°–94° C, which was shown by VPC analysis to be 85% cis-5-(2-bromobenzyloxy)-2-phenyl-1,3-dioxane and 11% trans-5-(2-bromobenzyloxy)-2-phenyl-1,3-dioxane.

EXAMPLE 11 cis-5-[2-Trifluoromethyl)benzyloxy]-2-phenyl-1,3-dioxane

Sodium hydride (4.0 g of 61%, 0.01 mole) was added to 5-hydroxy-2-phenyl-1,3-dioxane (18.0 g, 0.1 mole) in 150 ml of benzene. The slurry was stirred at ambient temperature for 1 hour and 2-(trifluoromethyl)benzyl bromide (23.9 g, 0.1 mole) was added. The slurry was heated at reflux for 15 hours, cooled and washed with water (2 × 100 ml). The organic layer was separated, dried over magnesium sulfate and concentrated to give 28.1 g of yellow oil which crystallized to give a solid, m.p. 58°–60° C. Recrystallization of the solid from benzene-ligroin gave 10.8 g (m.g. 65°–66° C), which on further recrystallization gave a solid, m.p. 68°–69° C. Analysis by VPC indicated this product to be essentially pure cis-5-[2-(trifluoromethyl)benzyloxy]-2-phenyl-1,3-dioxane.

EXAMPLE 12 cis-5-Benzyloxy-2-(3-methylphenyl)-1,3-dioxane

A. Preparation of 5-Hydroxy-2-(3-methylphenyl)-1,3-dioxane

A mixture of 3-methylbenzaldehyde (24.0 g, 0.2 mole), glycerol (18.4 g, 0.2 mole) and 40% sulfuric acid (2.0 ml) in 150 ml of benzene was heated under a Dean-Stark apparatus until no more water was collected (approximately 2.5 hours). The mixture was cooled, neutralized with potassium carbonate, diluted by the addition of 200 ml of ether and the ether solution washed with water (3 × 100 ml). The organic layer was dried over magnesium sulfate and concentrated to give a residue of 25.1 g of the desired 5-hydroxy-2-(3-methylphenyl)-1,3-dioxane $n_D^{25}$ 1.5346.

B. Preparation of 5-Benzyloxy-2-(3-methylphenyl)-1,3-dioxane

A slurry of sodium hydride (2.1 g. 0.08 mole in 100 ml of xylene and 100 ml of benzene was stirred at ambient temperature while 5-hydroxy-2-(3-methylphenyl)-1,3-dioxane (15.9 g, 0.08 mole) was added dropwise during 1 hour. Stirring was continued for one hour and to the mixture was added benzyl chloride (10.4 g, 0.08 mole) during 0.5 hour. This mixture was heated under reflux for 22 hours, cooled, filtered and the filtrate washed with water (2 × 250 ml). The washed solution was dried over magnesium sulfate and concentrated under reduced pressure to give 20.9 g of oil which distilled at 2 × 10$^{-4}$ mm. to give three fractions distilling respectively at 102°–133° C (cut 1); 133°–141° C (cut 2); and 141° C (cut 3). Analysis of the various cuts indicated that cut 3 was essentially pure cis-5-benzyloxy-2-(3-methylphenyl)-1,3-dioxane, 2.1 g, m.p. 68°–70° C and this cut was used in further studies.

EXAMPLE 13

5-Benzyloxy-2-(3-fluorophenyl)-1,3-dioxane

A. Preparation of 5-Hydroxy-2-(3-fluorophenyl)-1,3-dioxane

A mixture of 3-fluorobenzaldehyde (24.8 g, 0.2 mole), glycerol (18.4 g, 0.2 mole) and 40% sulfuric acid (2.0 ml) in benzene (200 ml) was heated with stirring under a Dean-Stark apparatus until water ceased to collect (approximately 2.5 hours). The mixture was cooled, neutralized with potassium carbonate and, after adding 200 ml of ether, washed with water (3 × 100 ml). The washed solution was dried over magnesium sulfate and concentrated under reduced pressure to give 29.0 g of colorless oil which was distilled under 0.025 mm using a short path distillation apparatus to give 18.9 g, $n_D^{24}$ 1.5160, of 5-hydroxy-2-(3-fluorophenyl)-1,3-dioxane which distilled at a bath temperature of 86°–105° C.

B. Preparation of 5-Benzyloxy-2-(3-fluorophenyl)-1,3-dioxane

A slurry of sodium hydride (3.7 g of 62%, 0.096 mole) in benzene (100 ml) and xylene (100 ml) was stirred at ambient temperature while 5-hydroxy-2-(3-fluorophenyl)-1,3-dioxane (18.9 g, 0.096 mole) was added dropwise during 1 hour. This mixture was stirred 1 additional hour, then to it was added benzyl chloride (12.2 g, 0.096 mole) during ½ hour. The mixture was heated under reflux for 18 hours, cooled, filtered and the filtrate washed with water (2 × 200 ml). The washed solution was dried over magnesium sulfate and concentrated to give 19.7 g of oil which was distilled under 2 × 10$^{-4}$ mm pressure to give three fractions distilling at bath temperature of 98°–119° C (cut 1); 119°–139° C (cut 2); and 139°–143° C (cut 3). Cut 2 (9.1 g) was found by nmr analysis to be a mixture of cis and trans-dioxanes and the corresponding dioxolane. Cut 3 (1.5 g, m.p. 70°–71° C) was found by nmr to be 100% cis-5-benzyloxy-2-(3-fluorophenyl)-1,3-dioxane and this cut was used in further studies.

EXAMPLE 14

5-(2-Fluorobenzyloxy)-2-(3-chlorophenyl)-1,3-dioxane

A. Preparation of 5-Hydroxy-2-(3-chlorophenyl)-1,3-dioxane

A mixture of 3-chlorobenzaldehyde (28.1 g, 0.2 mole), glycerol (18.4 g, 0.2 mole) and p-toluenesulfonic acid (0.1 g) in 150 ml of benzene was heated at reflux under a Dean-Stark apparatus until water was no longer collecting (3.6 ml). The solution was cooled, washed with 2% sodium bicarbonate solution (2 × 100 ml) and with water (2 × 100 ml). The washed solution was dried over magnesium sulfate and concentrated under reduced pressure. The oil remaining was distilled to give 18.1 g of colorless liquid which distilled at a pot temperature of 124°–128° C under 1 × 10$^{-4}$ mm.

B. Preparation of cis-5-(2-Fluorobenzyloxy)-2-(3-chlorophenyl)-1,3-dioxane

Sodium hydride (4.0 g of 60%, 0.1 mole) was added in small portions to a solution of 5-hydroxy-2-(3-chlorophenyl)-1,3-dioxane (21.5 g, 0.1 mole) in a mixture of 75 ml of benzene and 75 ml of xylene. After all sodium hydride had been added, the slurry was stirred at ambient temperature for ½ hour. To the mixture was added dropwise during fifteen minutes 2-fluorobenzyl chloride (14.4 g, 0.1 mole) and the mixture was heated under reflux for 10 hours. The mixture was cooled, washed with water (2 × 100 ml), dried over magnesium sulfate and concentrated under reduced pressure. The oil which remained was crystallized from benzene-ligroin to give 3.6 g of solid, m.p. 73°–75° C. Analysis by nmr indicated the product to be essentially pure cis-5-(2-fluorobenzyloxy)-2-(3-chlorophenyl)-1,3-dioxane. Recrystallization gave a solid, m.p. 85°–86° C.

EXAMPLE 15

5-(2-Fluorobenzyloxy)-2-(3-fluorophenyl)-1,3-dioxane

Using the procedure of Example 8, 5-hydroxy-2-(3-fluorophenyl)-1,3-dioxane (16.8 g, 0.085 mole) in 150 ml of benzene was reacted with sodium hydride (3.4 g of 60%) and the sodium salt thus formed was reacted with 2-fluorobenzyl chloride (12.3 g, 0.085 mole) to give 22.4 g of oil which was distilled under 1 × 10$^{-4}$ mm to give 11.4 g of product. Redistillation under 1 × 10$^{-4}$ mm gave three fractions which distilled at pot temperatures of 138°–145° C (cut 1), 145°–150° C (cut 2) and 150°–152° C (cut 3). Cuts 2 and 3 were combined (4.0 g) and the combined product found by nmr analysis to contain 30% cis-5-(2-fluorobenzyloxy)-2-(3-fluorophenyl)-1,3-dioxane.

EXAMPLE 16

5-Benzyloxy-2-(3-benzyloxyphenyl)-1,3-dioxane

A mixture of 2-benzyloxy-1,3-propanediol (18.0 g, 0.1 mole), 3-benzyloxybenzaldehyde (21.2 g, 0.1 mole) and p-toluenesulfonic acid (0.1 gram) in 150 ml of benzene was heated at reflux under a Dean-Stark apparatus until collection of water ceased (1.8 ml). The solution was washed with 2% sodium bicarbonate (2 × 100 ml) and with water (2 × 100 ml), then dried over magnesium sulfate and concentrated to give 34.2 g of brown oil. Recrystallization from benzene-ligroin gave 22.5 g of solid, m.p. 77°–78° C. nmr analysis of this solid indicated it to contain 31% cis-5-benzyloxy-2-(3-benzyloxyphenyl)-1,3-dioxane.

EXAMPLE 17

5-(2-Methylbenzyloxy)-2-(3chlorophenyl)-1,3-dioxane

Using the procedure of Example 9, 5-hydroxy-2-(3-chlorophenyl)-1,3-dioxane (21.5 g, 0.1 mole) was reacted with 2-methylbenzyl chloride (14.0 g, 0.1 mole) to give a heavy oil, which on distillation under 1 × 10$^{-4}$ mm pressure gave 12.5 g of product which distilled at a pot temperature of 160°–170° C. Analysis by nmr indicated this product to contain 18% cis-5-(2-methylbenzyloxy)-2-(3-chlorophenyl)-1,3-dioxane.

EXAMPLE 18

5-(4-Methylbenzyloxy)-2-phenyl-1,3-dioxane cis-5-Hydroxy-2-phenyl-1,3-dioxane (16.8 g, 0.1 mole) was reacted with 4-methylbenzyl chloride (14.0 g, 0.1 mole) using the procedure of Example 2. When the reaction mixture had cooled, solid began to separate, thus the entire reaction mixture was concentrated under reduced pressure. The solid product was slurried with water and filtered. The filter cake was dried in a vacuum oven to give 23.2 g of solid, m.p. 106°–109° C. Recrystallization from benzene-ligroin gave 9.1 g, m.p. 109°–110° C. A second recrystallization raised the m.p. to 112.5°–113° C. Analysis by VPC indicated the product thus obtained was nearly pure cis-5-(4-methylbenzyloxy)-2phenyl-1,3-dioxane.

EXAMPLE 19

5-Benzyloxy-2-(3-chlorophenyl)-1,3-dioxane

A slurry of 5-hydroxy-2-(3-chlorophenyl)-1,3-dioxane (21.5 g, 0.1 mole) in 200 ml of xylene was stirred at ambient temperature while sodium hydride (4.0 g of 61%) was added in small portions. When all the hydride had been added, the slurry was stirred for an additional ½ hour. Benzyl chloride (14.2 g, 0.1 mole) was added dropwise during 15 minutes to the stirred mixture and the slurry was then heated at 100° C for 10 hours. The mixture was cooled to room temperature, washed with water (2 × 100 ml), dired over magnesium sulfate and concentrated. The oil which remained (20.2 g) was recrystallized from benzene-ligroin to give 4.8 g of solid, m.p. 83°–84° C. Recrystallization gave a solid, m.p. 85°–85.5° C. Analysis by VPC indicated this product to be 97% cis-5-benzyloxy-2-(3-chlorophenyl)-1,3-dioxane.

EXAMPLE 20

5Benzyloxy-2-(2-fluorophenyl)-1,3-dioxane

A. Preparation of 2-(2-Fluorophenyl)-5-hydroxy-1,3-dioxane

A mixture of 2-fluorobenzaldehyde (24.8 g, 0.2, mole), glycerol (18.4 g, 0.2 mole) and 40% sulfuric acid (2 ml) was heated at 80°–100° C for 12 hours. The mixture cooled to room temperature and 100 ml of ether was added. The solution was washed with 2% potassium carbonate solution, dried over magnesium sulfate and concentrated under reduced pressure. The oil which remained (28.7 g) was distilled under 1 × 10$^{-5}$mm to give a product (18 g) which distilled at a pot temperature of 140°–145° C. This product was identified by infrared and elemental analysis as 5-hydroxy-2-(2-fluorophenyl)-1,3-dioxane.

B. Preparation of 5-Benzyloxy-2-(2-fluorophenyl)-1,3-dioxane

5-Hydroxy-2-(2-fluorophenyl)-1,3-dioxane (18.0 g, 0.09 mole) was reacted with sodium hydride and benzyl chloride (13.0 g, 0.09 mole) as described in Example 2, except that the slurry was heated at 80°–100° C for 12 hours. The product was isolated in the manner described in Example 2 to give 12.1 g of oil which was distilled under 1 × 10$^{-5}$ mm to give a product (6.2 g) which distilled at a pot temperature of 165°–170° C. VPC analysis of this product indicated it to contain 32% cis-5-benzyloxy-2-(2-fluorophenyl)-1,3-dioxane.

EXAMPLE 21

5-Benzyloxy-2-(3-methoxyphenyl)-1,3-dioxane

Using the method of Example 16, 2-benzyloxy-1,3-propane-diol (18.0 g, 0.1 mole), and 3-methoxybenzaldehyde (13.6 g, 0.1 mole) were reacted to give 26.0 g of oil which was distilled at 1 × 10$^{-4}$ mm to give 20.2 g of product which distilled at a pot temperature of 200°–206° C. nmr analysis of this product indicated it to contain 37% cis-5-benzyloxy-2-(3-methoxyphenyl)-1,3-dioxane.

EXAMPLE 22

5-(2-Methoxybenzyloxy)-2-phenyl-1,3-dioxane

5-Hydroxy-2-phenyl-1,3-dioxane (8.4 g, 0.05 mole) was reacted with sodium hydride and 2-methoxybenzyl chloride (7.8 g, 0.05 mol) according to the method of Example 2, except that the mixture was heated at 100° C for 12 hours, to give 11.7 g of yellow oil. The oil was distilled under $1 \times 10^{-5}$ mm to give 4.6 g of product, which distilled at a pot temperature of 180°–190° C. VPC analysis of the product showed it to contain 72% cis-5-(2methoxybenzyloxy)-2-phenyl-1,3-dioxane.

EXAMPLE 23 cis-5-(2,5-Dimethylbenzyloxy)-2-phenyl-1,3-dioxane

5-Hydroxy-2-phenyl-1,3-dioxane (8.4 g, 0.05 mole) was reacted with sodium hydride and 2,5-dimethylbenzyl chloride (7.9 g, 0.05 mole) according to the method of Example 2, except that the mixture was held at 100° C for 6 hours. On concentration of the washed mixture, 14.7 g of solid, m.p. 93°–98° C, was obtained. Recrystallization from benzene-ligroin gave 5.9 g, m.p. 102°–103° C. VPC analysis of this solid indicated it to contain 100% cis-5-(2,5-dimethylbenzyloxy)-2-phenyl-1,3-dioxane.

EXAMPLE 24

Pre-emergence Herbicidal Activity of Substituted 5-Benzyloxy-1,3-Dioxanes

Employing the general method described in Example 1, the herbicidal activity of substituted 5-benzyloxy-1,3-dioxanes was assessed. The results obtained are presented in Table 3.

Table 3

| Compound of Example | Plant Species | Preemergence Herbicidal Activity of Substituted 5-Benzyloxy-1,3-dioxanes (response at indicated rate) Rate in Pounds per Acre | | | | | | | | |
|---|---|---|---|---|---|---|---|---|---|---|
| | | 0.375 | 0.5 | 0.75 | 1.0 | 1.5 | 2.0 | 3.0 | 4.0 | 6.0 | 8.0 |
| 7* | Crabgrass | 100 | | $50^b$ | | 100 | | 100 | | 100 | |
| | Flax | 0 | | $0^c$ | | $0^c$ | | $0^b$ | | $0^b$ | |
| | Corn | 0 | | 0 | | 0 | | $60^c$ | | $20^c$ | |
| | Mustard | 0 | | 0 | | 0 | | 0 | | 0 | |
| | Tomato | 0 | | 0 | | 0 | | 0 | | 0 | |
| | Barnyardgrass | $30^b$ | | $30^b$ | | $80^b$ | | 100 | | 100 | |
| | Wheat | | | 0 | | 0 | | 0 | | | |
| | Wild Oats | | | 0 | | 0 | | 0 | | | |
| | Rice | | | 30 | | 80 | | $80^c$ | | | |
| 8* | Corn | | | 0 | | $20^c$ | | $60^c$ | | 100 | |
| | Barnyardgrass | $25^c$ | | $75^b$ | | 100 | | 100 | | 100 | |
| | Wheat | | | 0 | | $0^c$ | | $30^c$ | | | |
| | Wild Oats | | | | | $10^c$ | | $10^c$ | | | |
| | Rice | | | 100 | | 100 | | 100 | | | |
| | Crabgrass | $50^c$ | | $90^a$ | | 100 | | 100 | | 100 | |
| | Mustard | 0 | | 0 | | 0 | | 0 | | $20^c$ | |
| | German hay millet | $90^c$ | | $95^b$ | | 100 | | 100 | | 100 | |
| | Chickweed | $90^c$ | | $90^b$ | | 100 | | 100 | | 100 | |
| 9* | Crabgrass | $80^c$ | | 100 | | 100 | | 100 | | 100 | |
| | Mustard | 0 | | 0 | | 0 | | $0^c$ | | $0^b$ | |
| | Barnyardgrass | $40^c$ | | $50^c$ | | 100 | | 100 | | 100 | |
| | German hay millet | 100 | | 100 | | 100 | | 100 | | 100 | |
| | Corn | 40 | | 40 | | 80 | | 100 | | 100 | |
| | Chickweed | 100 | | 100 | | 100 | | 100 | | 100 | |
| 10** | Crabgrass | | | $90^c$ | | 100 | | 100 | | 100 | |
| | Kochia | | | 0 | | $0^c$ | | $20^c$ | | $30^c$ | |
| | Chickweed | | | $70^c$ | | $75^b$ | | $50^b$ | | $50^b$ | |
| | Barnyardgrass | | | 100 | | 100 | | 100 | | 100 | |
| | Mustard | | | 0 | | 0 | | $0^c$ | | $0^c$ | |
| | Corn | | | $80^c$ | | 100 | | 100 | | 100 | |
| 11* | Corn | | $20^c$ | | $20^c$ | | $80^b$ | | $60^b$ | | |
| | Mustard | | 0 | | 0 | | 0 | | 0 | | |
| | Crabgrass | | $20^c$ | | $30^c$ | | $70^c$ | | $80^b$ | | |
| | Barnyardgrass | | $80^c$ | | $90^b$ | | 100 | | 100 | | |
| | Cotton | | 0 | | 0 | | 0 | | 0 | | |
| 12* | Corn | $0^c$ | | | 0 | | $60^b$ | | $80^b$ | | |
| | Mustard | | 0 | | 0 | | 0 | | 20 | | |
| | Crabgrass | | 100 | | 100 | | $95^a$ | | 100 | | |
| | Barnyardgrass | | 100 | | 100 | | $95^a$ | | 100 | | |
| | Cotton | | 0 | | 0 | | 0 | | 0 | | |
| 13* | Corn | | 100 | | 100 | | 100 | | 100 | | |
| | Mustard | | 0 | | 0 | | 0 | | 0 | | |
| | Crabgrass | | 100 | | 100 | | 100 | | 100 | | |
| | Barnyardgrass | | 100 | | 100 | | 100 | | 100 | | |
| | Cotton | | 0 | | 0 | | 0 | | 0 | | |
| 14* | Corn | | $60^b$ | | 100 | | 100 | | 100 | | 100 |
| | Mustard | | 0 | | 0 | | 0 | | 0 | | 0 |
| | Crabgrass | | 100 | | 100 | | 100 | | 100 | | 100 |
| | Barnyardgrass | | $70^a$ | | $80^a$ | | 100 | | $95^a$ | | $90^a$ |
| | Cotton | | 0 | | 0 | | 0 | | 0 | | 0 |
| 15** | Corn | | 100 | | 100 | | 100 | | 100 | | 100 |
| | Mustard | | 0 | | 0 | | 0 | | 0 | | $0^c$ |
| | Crabgrass | | 100 | | 100 | | 100 | | 100 | | 100 |
| | Barnyardgrass | | 100 | | 100 | | $90^a$ | | 100 | | 100 |
| | Cotton | | 0 | | 0 | | 0 | | 0 | | 0 |
| 16** | Corn | | | | 0 | | $0^c$ | | $0^c$ | | $0^c$ |
| | Mustard | | | | 0 | | 0 | | 0 | | 0 |
| | Crabgrass | | | | $60^c$ | | $50^c$ | | $50^b$ | | $70^b$ |
| | Barnyardgrass | | | | $60^c$ | | $60^c$ | | $50^b$ | | $70^b$ |
| | Cotton | | | | 0 | | 0 | | 0 | | 0 |
| 17** | Corn | | 0 | | 0 | | $0^c$ | | $20^b$ | | $40^b$ |
| | Mustard | | 0 | | 0 | | 0 | | 0 | | $0^c$ |
| | Crabgrass | | $50^b$ | | $80^a$ | | 100 | | 100 | | 100 |
| | Barnyardgrass | | $50^b$ | | $80^a$ | | 100 | | 100 | | 100 |
| | Cotton | | 0 | | 0 | | 0 | | 0 | | 0 |
| 18* | Lamb's quarter | | | | 0 | | 0 | | 0 | | 0 |
| | Dallis grass | | | | 0 | | 0 | | 0 | | 20 |
| | Chickweed | | | | 0 | | 0 | | 0 | | $10^b$ |

Table 3-continued
Preemergence Herbicidal Activity of Substituted 5-Benzyloxy-1,3-dioxanes
(response at indicated rate)

| Compound of Example | Plant Species | Rate in Pounds per Acre | | | | | | | | | |
|---|---|---|---|---|---|---|---|---|---|---|---|
| | | 0.375 | 0.5 | 0.75 | 1.0 | 1.5 | 2.0 | 3.0 | 4.0 | 6.0 | 8.0 |
| | Tomato | | | | 0 | 0 | | 0 | | 0 | |
| | Sugar beets | | | | 0 | 0 | | 0 | | 0 | |
| | Giant foxtail | | | | 60$^c$ | 50$^c$ | | 90$^c$ | | 70$^c$ | |
| | Wild Oats | | | | 0 | 0 | | 0 | | 0 | |
| | Downy brome | | | | 0 | 0 | | 0 | | 0 | |
| | Lima beans | | | | 0 | 0 | | 0 | | 0 | |
| | Carrots | | | | 0 | 0 | | 0 | | 0$^c$ | |
| | Alfalfa | | | | 0 | 0 | | 0 | | 0 | |
| | Peppers | | | | 0 | 0 | | 0 | | 0 | |
| | Cucumber | | | | 0 | 0 | | 0 | | 0 | |
| | Corn | | | | 0 | 0 | | 0 | | 0 | |
| | Mustard | | | | 0 | 0 | | 0 | | 0 | |
| | Lettuce | | | | 0 | 0 | | 0 | | 0 | |
| | Crabgrass | | | | 50$^c$ | 70$^c$ | | 100 | | 100 | |
| | Cotton | | | | 0 | 0 | | 0 | | 0 | |
| | Rice | | | | 0 | 0 | | 0 | | 25$^c$ | |
| | Barnyardgrass | | | | 20$^c$ | 70$^c$ | | 100 | | 100 | |
| | German hay millet | | | | 60$^c$ | 70$^c$ | | 100 | | 75$^c$ | |
| | Wheat | | | | 0 | 0 | | 0 | | 0 | |
| 19* | Corn | | | | 40$^c$ | 60$^c$ | | 100 | | 100 | |
| | Crabgrass | | | | 100 | 95$^a$ | | 100 | | 100 | |
| | Barnyardgrass | | | | 40$^a$ | 95$^c$ | | 100 | | 100 | |
| | Cotton | | | | 0 | 0 | | 0 | | 0 | |
| | Mustard | | | | 0 | 0 | | 0 | | 0 | |
| | Lima Beans | | | | 0 | 0 | | 0 | | 0 | |
| 20* | Lima Beans | | | | | 0 | | 0 | | 0 | |
| | Corn | | | | | 50$^c$ | | 50$^c$ | | 100 | |
| | Mustard | | | | | 0 | | 0 | | 0 | |
| | Lettuce | | | | | 0 | | 0 | | 0 | |
| | Crabgrass | | | | | 90$^c$ | | 100 | | 100 | |
| 21** | Corn | | 40$^c$ | | 40$^b$ | | 80$^a$ | | 100 | | 100 |
| | Mustard | | 0 | | 0 | | 0 | | 0 | | 0 |
| | Crabgrass | | 100 | | 100 | | 100 | | 100 | | 100 |
| | Barnyardgrass | | 80 | | 50$^b$ | | 95$^a$ | | 100 | | 100 |
| | Cotton | | 0 | | 0 | | 0 | | 0 | | 0 |
| 22* | Corn | | | | 0 | | | 0$^c$ | | 100 | |
| | Barnyardgrass | | | | 20$^c$ | 40$^b$ | | 80$^a$ | | 80$^a$ | |
| | Crabgrass | | | | 40$^b$ | 60$^a$ | | 100 | | 100 | |
| | Mustard | | | | 0 | 0 | | 0 | | 0$^c$ | |
| | Chickweed | | | | 20 | 60$^c$ | | 90$^c$ | | 90$^c$ | |
| 23* | Corn | | | | 0 | 0 | | 0 | | 0 | |
| | Mustard | | | | 0 | 0 | | 0 | | 0 | |
| | Crabgrass | | | | 0 | 0 | | 30 | | 75$^c$ | |
| | Barnyardgrass | | | | 0 | 0 | | 20 | | 70$^c$ | |
| | German hay millet | | | | 0 | 0 | | 50 | | 90$^c$ | |

*Rate is as produced, without consideration of cis content.
**Rate is that of cis isomer applied.
$^a$Surviving plants are so severely injured that they will not survive.
$^b$Surviving plants are severely injured and probably will not survive.
$^c$Surviving plants are injured but will probably survive.

EXAMPLE 25

Post-emergence Herbicidal Activity of Substituted 5-Benzyloxy-1,3-dioxanes

Employing the method described in Example 1, but applying the materials at six pounds per acre, the post-emergence herbicidal activity of selected substituted 5-benzyloxy-1,3-dioxanes was assessed using as test species corn, mustard, crabgrass and barnyardgrass. The results of these tests are presented in Table 4.

Table 4
Post-emergence Acitivity of Substituted 5-Benzyloxy-1,3-dioxanes
(response at 6 pounds per acre)

| Compound of Example | RESPONSE | | | |
|---|---|---|---|---|
| | Corn | Mustard | Crabgrass | Barnyardgrass |
| 7* | 0 | 0 | 0$^a$ | 0$^b$ |
| 8* | 0$^a$ | 0 | 100 | 100 |
| 10** | 0$^c$ | 0 | 60$^a$ | 20$^c$ |
| 12*** | 0$^c$ | 0 | 20$^c$ | 80$^c$ |
| 18* | 0 | 0$^a$ | | 10$^c$ |

*Rate is as produced, without consideration of cis content.
**Rate is that of cis isomer applied.
***Applied at four pounds per acre only.
$^a$Surviving plants are so severely injured that they will not survive.
$^b$Surviving plants are severely injured and probably will not survive.
$^c$Surviving plants are injured, but will probably survive.

EXAMPLE 26

Herbicidal Activity of 5-(2-fluorobenzyloxy)-2-phenyl)-1,3-dioxane and 5-Benzyloxy-2-(3-fluorophenyl)-1,3-dioxane Employing the method of Example 1, but using low rates of application, the pre- and post-emergence herbicidal activity of 5-(2-fluorobenzyloxy)-2-phenyl-1,3-dioxane (compound of Example 9) and 5-benzyloxy-2-(3-fluorophenyl)-1,3-dioxane (compound of Example 13) was asessed using as test species a number of important crop and weed species. Results are tabulated in Tables 5 and 6.

Table 5
Pre-emergence Herbicidal Activity of 5-(2-Fluorobenzyloxy)-2-phenyl-1,3-dioxane and 5-Benzyloxy-2-(3-fluorophenyl)-1,3-dioxane

| SPECIES | Compound of Example 9* | | | Compound of Example 13* | | |
|---|---|---|---|---|---|---|
| Rate (lb/acre) | 0.5 | 1.0 | 2.0 | 0.5 | 1.0 | 2.0 |
| Lima beans | 0 | 0 | 0 | 0 | 0 | 0 |
| Corn | 80$^a$ | 100 | 100 | 80$^c$ | 100 | 100 |
| Mustard | 0 | 0 | 0 | 0 | 0 | 0 |
| Crabgrass | 100 | 100 | 100 | 100 | 100 | 100 |
| Barnyardgrass | 100 | 100 | 100 | 100 | 100 | 100 |
| Cotton | 0 | 0 | 0 | 0 | 0 | 0 |
| Tomato | 0 | 0 | 0 | 0 | 0 | 0 |
| Rice | 100 | 100 | 100 | 100 | 100 | 100 |
| Red clover | 30 | 40 | 70$^c$ | 60$^c$ | 0 | 50$^c$ |
| Wild oats | 50$^c$ | 60$^c$ | 90$^b$ | 30 | 70$^c$ | 50$^c$ |
| Peas | 20 | 10 | 20 | 20 | 10$^c$ | 10$^c$ |

*Rate is as produced, without consideration of cis content.
$^a$Surviving plants are so severely injured that they will not survive.
$^b$Surviving plants are severely injured and probably will not survive.
$^c$Surviving plants are injured, but will probably survive.

Table 6
Post-emergence Herbicidal Activity of Substituted 5-Benzyloxy-1,3-dioxanes

| Compound of Example | Species | Rate in Pounds per Acre | | | |
|---|---|---|---|---|---|
| | | 0.5 | 1.0 | 2.0 | 4.0 |
| 9* | Corn | 0$^c$ | 20$^c$ | 100 | 100 |
| | Mustard | 0 | 0 | 0 | 0$^c$ |
| | Crabgrass | 20$^c$ | 20$^a$ | 100 | 100 |
| | Barnyardgrass | 80$^c$ | 40$^a$ | 95 | 100 |
| | Cotton | 0 | 0 | 0$^c$ | 0$^c$ |
| 13* | Corn | 20$^c$ | 0$^c$ | 0$^a$ | 100 |
| | Mustard | 0 | 0 | 0 | 0 |
| | Crabgrass | 0$^c$ | 0$^a$ | 20$^a$ | 100 |
| | Barnyardgrass | 40 | 90$^a$ | 80$^b$ | 100 |
| | Cotton | 0 | 0 | 0$^c$ | 0$^c$ |

*Rate is as produced, without consideration of cis content.
$^a$Surviving plants are so severely injured that they will not survive.
$^b$Surviving plants are severely injured and probably will not survive.
$^c$Surviving plants are injured, but will probably survive.

EXAMPLE 27

5-Benzyloxy-2-methyl-1,3-dioxane

A. Preparation of 5-Hydroxy-2-methyl-1,3-dioxane

In a 500 ml three-necked flask equipped with stirrer, condenser and Dean-Stark trap (for azeotropic removal of water) 44 g acetaldehyde was slowly added to a stirrer mixture of 92 g glycerol and six drops of concentrated sulfuric acid. The reaction mixture was heated at 100° C for 3 hours, then cooled to room temperature and neutralized with solid potassium carbonate. The mixture was washed with 100 ml of petroleum ether and the distilled at 58°–60°/0.75 mm Hg to give 68.4 g of a mixture of dioxanes and dioxolanes.

A portion of the dioxane/dioxolane mixture was treated with about 0.6 g of hydrogen chloride gas and then heated on a steam for ½ hour. After the mixture was cooled to room temperature, 150 ml of dry pyridine was added. To this mixture was slowly added 71 g of benzoyl chloride, and the resultant suspension was stirred for 1 hour at room temperature. The reaction mixture was then poured into 1.5 liters of cold water, and an oil separated out. The aqueous layer was extracted with two 200-ml volumes of ether and the ether extracts added to the oil. This organic mixture was washed sequentially with two 100-ml volumes of 5% sodium hydroxide, two 100-ml volumes of 3% sulfuric acid, and water. After the ether solution was dried over potassium carbonate, the solvent was removed by evaporation. Petroleum ether (100 ml) was added to the residual oil, and upon refrigeration of the resulting suspension, 14.4 g of 5-benzoyloxy-2-methyl-1,3-dioxane (m.p. 76°–78° C) precipitated.

To hydrolyze the benzoyloxy-1,3-dioxane, 1.8 g of sodium in 25 ml of methanol was added in portions to a stirred mixture of 14.0 g of 5-benzoyloxy-2-methyl-1,3-dioxane and 80 ml of chloroform. The reaction mixture was stirred at 60° C for 48 hours, then cooled to room temperature and neutralized with solid carbon dioxide. After solvents were removed under reduced pressure, the residue was dissolved in water. The solution was washed with petroleum ether and then extracted with ether. After the ether extract was dried over magnesium sulfate, ether was removed under pressure to yield 5.1 g of 5-hydroxy-2-methyl-1,3-dioxane. The infrared spectrum of the product was consistent with the assigned structure.

B. Preparation of 5-Benzyloxy-2-methyl-1,3-dioxane

To a mixture of 4.8 g of 5-hydroxy-2-methyl-1,3-dioxane and 100 ml of benzene in a 250 ml three-necked flask equipped with stirrer, condenser, thermometer and powder funnel was added 1.6 g of sodium hydride in portions. This mixture was stirred at room temperature for ½ hour after which 5.1 g of benzyl chloride was added in portions (over a 15 minute period). The reaction mixture was heated, with stirring, at 80° C for 24 hours. The reaction mixture was washed with two 100-ml volumes of water, and the organic layer was then dried over magnesium sulfate. Solvent was removed under reduced pressure to give 7.5 g of oil, which was distilled to give 4.1 g of 5-benzyloxy-2-methyl-1,3-dioxane; b.p. 111°–112° C.0.4 mm Hg; $n_D^{25}$ 1.5013. The ir and nmr spectra were consistent with the assigned structure and showed the product to consist of 70% cis and 30% trans isomer.

Analysis: Calc'd for $C_{12}H_{16}O_3$: C 69.21; H 7.74; Found: C 68.97; H 7.76.

EXAMPLE 28

5-Benzyloxy-2-ethyl-1,3-dioxane

By the method of Example 27 propionaldehyde was condensed with glycerol, and the resulting intermediate was purified by the formation of the benzoate, 5-benzoyloxy-2-ethyl-1,3-dioxane, m.p. 62°–68.5° C. The benzoate was hydrolyzed by the method of Example 27 to yield 2-ethyl-5-hydroxy-1,3-dioxane, b.p. 94°–97° C/23–25 mm Hg. By the method of Example 27 the intermediate 5-hydroxy compound was converted to 5-benzyloxy-2-ethyl-1,3-dioxane, b.p. 85°–91° C/0.025–0.03 mm Hg, $n_D^{25}$ 1.5050. The ir and nmr spectra of the product were consistent with the assigned structure and showed the product to consist of 90% cis isomer.

Analysis: Calc'd for $C_{13}H_{18}O_3$: C 70.24; H 8.16; Found: C 70.47; H 8.16.

By the method of Example 27 the following compounds were prepared:

EXAMPLE 29

5-(2-Fluorobenzyloxy)-2-methyl-1,3-dioxane, b.p. 70°–74° C/$10^{-4}$ mm Hg. The ir and nmr spectra of the product were consistent with the assigned structure and showed the product to be 90% cis isomer.

Analysis: Calc'd for $C_{12}H_{15}FO_3$: C 63.79; H 6.88; Found: C 63.69; H 6.94.

EXAMPLE 30

2Methyl-5-(2-methylbenzyloxy)-1,3-dioxane, b.p. 110°–114° C/10$^{-4}$mm Hg. The ir and nmr spectra of the product were consistent with the assigned structure and showed the product to consist of 60% cis and 40% trans isomer.

Analysis: Calc'd for $C_{13}H_{18}O_3$: C 70.24; H 8.16; Found: C 70.47; H 8.27.

EXAMPLE 31

2-Ethyl-5-(2-fluorobenzyloxy)-5-methyl-1,3-dioxane

A. Preparation of 2-(2-Fluorobenzyloxy)-2-methyl-1,3-propanediol

In a two-liter flask equipped with stirring bar, thermometer, dropping funnel, and condenser with drying tube 88.4 g of 2-fluorobenzyl alcohol was added dropwise over a period of 45 minutes to a stirred suspension of 20.2 g of sodium hydride in 1200 ml of anhydrous toluene. After the addition was carried out at 25°–30° C, the reaction mixture was heated at 90° C for 1½ hours, then cooled, and 177.1 g of diethyl 2-bromo-2-methylmalonate was added over 1¼ hours at 30°–50° C. The reaction mixture was heated at 90°–95° C for 2 hours and then allowed to cool and remain at room temperature overnight. The reaction mixture and 500 ml of ether were poured into a flask containing 1 liter of saturated sodium bicarbonate solution and 1 kg of crushed ice. After the ice had melted, the aqueous phase was separated and extracted with three 500-ml portions of ether. The ethereal solutions were combined, washed with three 500-ml portions of water, and dried by filtration through sodium sulfate. Removal of ether and residual toluene under reduced pressure gave 176.2 g of diethyl 2-(2-fluorobenzyloxy)-2-methylmalonate, identity confirmed by ir spectrum.

A suspension of 25.8 g of lithium aluminum hydride in 1000 ml of anhydrous ether was prepared in a 2-liter flask equipped with stirrer, dropping funnel, and condenser with drying tube. Diethyl 2-(2-fluorobenzyloxy)-2-methylmalonate (101.6 g) was added to the stirred suspension at a rate sufficient to maintain refluxing. When the addition was complete, the dropping funnel was rinsed with 100 ml of ether, and the reaction mixture was refluxed for 4 more hours. The mixture was cooled and kept in an ice bath while excess reducing agent was decomposed by dropwise addition of saturated sodium sulfate solution. Ice-water (250 ml) and 1150 ml of 10% sulfuric acid were then added to the stirred reaction mixture. The aqueous phase was separated from the ether solution, saturated with sodium chloride, and extracted with two 500-ml portions of ether. The ether solutions were combined, dried over sodium sulfate, and concentrated to an oil. Distillation at 0.01 mm Hg removed volatile impurities, leaving a residue which was recrystallized from petroleum ether-chloroform to give 27.5 g of 2-(2-fluorobenzyloxy)-2-methyl-1,3-propanediol, m.p. 74.5°–75° C. The ir and nmr spectra were consistent with the assigned structure.

Analysis: Calc'd for $C_{11}H_{14}FO_3$: C 61.66; H 7.06; Found: C 61.44; H 6.95.

B. Preparation of 2-Ethyl-5-(2-fluorobenzyloxy)-5-methyl-1,3-dioxane

A mixture of 9.4 g of 2-(2-fluorobenzyloxy)-2-methyl-1,3-propanediol, 2.8 g of propionaldehyde, 300 ml of hexane, and a catalytic amount of p-toluenesulfonic acid was refluxed for 2 hours in a 500 ml flask equipped with stirrer, Dean-Stark trap, and condenser with drying tube. After standing overnight the reaction mixture was filtered, and the filtrate was concentrated under reduced pressure to an oil which was dissolved in 300ml of benzene. The benzene solution was washed with 100 ml of 10% sodium carbonate and two 100-ml portions of water, dried over sodium sulfate, and then concentrated under reduced pressure to an oil. The oil was placed on a silica gel column (30 × 310 cm) and eluted first with petroleum ether (fractions 1–3), then with petroleum ether-ethyl acetate (99:1 for fractions 4–19 and 9:1 for fractions 20–23). Fraction 1 was 200 ml, fractions 2, 3, 24 and 25 were 100 ml each, and fractions 4–23 were 50 ml each; elution was monitored by thin layer chromatography. Product recovered from fractions 9–12 was distilled to give 2.0 g of r-2-ethyl-t-5-(2-fluorobenzyloxy)-5-methyl-1,3-dioxane; b.p. 78°–79° C/4 × 10$^{-4}$ mm Hg; $n_D^{25}$ 1.4878. Product from fractions 15–25 was distilled to give 3.7 g of r-2-ethyl-c-5-(2-fluorobenzyloxy)-5-methyl-1,3-dioxane; b.p. 82°–86° C/4 × 10$^{-4}$ mm Hg; $n_D^{25}$ 1.4909. The ir and nmr spectra of each isomer were consistent with the assigned conformation and showed each to be free of the other isomer. The purity was further confirmed by thin-layer chromatographic analysis.

Analysis: Calc'd for $C_{14}H_{19}FO_3$: C 66.12; H 7.53; Found (t-isomer): C 66.30; H 7.62; Found (c-isomer): C 66.08; H 7.65.

EXAMPLE 32

2-Ethyl-5-(2-methylbenzyloxy)-5-methyl-1,3-dioxane

A. Preparation of 2-ethyl-5-methylene-1,3-dioxane

In a 2-liter flask equipped with a stirrer, Dean-Stark trap, and condenser with drying tube, a mixture of 16.3 g of propionaldehyde, 20.2 g of 1-hydroxy-2-hydroxymethyl-2-propene, 0.16 of p-toluenesulfonic acid, and 1200 ml of hexane was stirred and heated under reflux for 2 hours, during which time 5.3 ml of water was collected in the Dean-Stark trap. The reaction mixture was concentrated under reduced pressure to a volume of about 50 ml, then taken up in 200 ml of ether. The ether solution was washed with 75 ml of 10% sodium carbonate and then twice with 75-ml portions of water. After drying over magnesium sulfate the ether solution was concentrated under reduced pressure to yield 26.5 g of yellow oil. The crude product was fractionated under reduced pressure to yield 21.5 g of 2-ethyl-5-methylene-1,3-dioxane, b.p. 68° C/41 mm Hg. The nmr spectrum was consistent with the assigned structure. The synthesis was later repeated, and the index of refraction of the product was found to be $n_D^{25}$ 1.4432.

B. Preparation of 6-ethyl-1,5,7-trioxaspiro[2.5]octane

In a 50 ml flask fitted with a stirrer, dropping funnel, thermometer, and condenser with drying tube were placed 5.0 g of 2-ethyl-5-methylene-1,3-dioxane, 4.1 g of benzonitrile, 4.3 g of potassium bicarbonate, and 25 ml of absolute methanol. The mixture was stirred at room temperature (25°–30° C) while 4 ml of 30% hydrogen peroxide was added dropwise over a period of 5 hours. After the addition was complete, the reaction mixture was stirred at room temperature overnight. To the reaction mixture was added 75 ml of water, and the aqueous solution was extracted three times with 40-ml portions of chloroform. The chloroform extracts were combined and washed with first 40 ml of 10% sodium carbonate solution, then with 40ml of water, and dried over sodium sulfate. The chloroform solution was concentrated almost to dryness under reduced pressure. The resulting slurry was filtered and the solid material washed with ether. The filtrate was concentrated to yield 6.1 g of clear liquid. An nmr spectrum showed that 50% of the methylene compound had been converted to the epoxide, 95% of the epoxide being of the desired form. This crude product was combined with another batch from a similar run for distillation. Fractional distillation yielded 4.8 g of a colorless liquid, b.p. 84°–95° C/11 mm Hg, shown by nmr spectrum to be a mixture containing the desired epoxidized methylene compound. This crude product was combined with 10.0 g of similarly prepared crude product and fractionally distilled (spinning band column) to yield 4.2 g of a colorless liquid b.p. 90°–91° C/11 mm Hg, $n_D^{25}$ 1.4505, which was shown by nmr spectroscopy to be essentially pure 6-ethyl-1,5,7-trioxaspiro[2,5]octane. The product was redistilled for analysis, b.p. 94° C/10mm Hg, $n_D^{25}$ 1.4505. The ir and nmr spectra were consistent with the assigned structure.

Analysis: Calc'd for $C_7H_{12}O_3$: C 58.31, H 8.39; Found: C 58.60; H 8.09.

C. Preparation of 2-Ethyl-5-hydroxy-5-methyl-1,3-dioxane

6-Ethyl-1,5,7-trioxaspiro[2.5]octane (7.6 g), 1.5 g of 10% palladium on carbon, and 75 ml of absolute ethanol were placed in a pressure bottle, and the mixture was hydrogenated at 45 psi and 25° for 1 hour, taking up 5 lbs of hydrogen. The solution was filtered and concentrated under reduced pressure to yield 6.8 g of clear liquid, which was taken up in 100 ml of ether, washed three times with 20-ml portions of water, and then dried over magnesium sulfate. The ether solution was concentrated under reduced pressure to yield 3.6 g of clear liquid. The water washings were saturated with sodium chloride and extracted three times with 50-ml portions of ether. These ether extracts were dried over magnesium sulfate and then concentrated under reduced pressure to yield 2.6 g of clear liquid. The organic portions were combined and fractionally distilled to yield 6.0 g of 2-ethyl-5-hydroxy-5-methyl-1,3-dioxane, b.p. 62° C/10 mm Hg, $n_D^{25}$ 1.4378. The ir and nmr spectra were consistent with the assigned structure and showed the product to be 95% cis isomer.

Analysis: Calc'd for $C_7H_{14}O_3$: C 57.51; H 9.65, Found: C 57.80; H 9.39.

D. Preparation of 2-Ethyl-5-(2-methylbenzyloxy)-5-methyl-1,3-dioxane

In a flask equipped with a stirrer, dropping funnel, thermometer, and condenser with drying tube 1.1 g of sodium hydride in 75 ml of dimethyl formamide was stirred while 5.9 g of 2-ethyl-5-hydroxy-5-methyl-1,3-dioxane in 25 ml of dimethylformamide was added dropwise over a period of ¾ hour. Stirring was continued for an additional 1½ hours, after which 6.2 g of 2-methylbenzyl chloride was added, and the reaction mixture was heated at 90°–95° C for 21 hours. The reaction mixture was concentrated to a volume of about 60 ml by distillation at 11 mm Hg. The concentrated reaction mixture was poured onto 200 g of ice and stirred until the ice had melted. A trace of white solid was filtered from the aqueous solution, and the solution was then extracted four times with 100-ml portions of ether. The ether extracts were combined, dried over magnesium sulfate, and concentrated under reduced pressure to yield 9.8 g of yellow liquid. This product was taken up in 175 ml of ether and washed three times with 50 ml of water. The ether solution was dried over magnesium sulfate and concentrated under reduced pressure to yield 8.4 g of amber liquid. Fractional distillation yielded 4.8 g of colorless liquid, r-2-ethyl-c-5-(2-methylbenzyloxy)-5-methyl-1,3-dioxane, b.p. 82.5° C/0.14 mm Hg, $n_D^{25}$ 1.5075. The nmr and ir spectra were consistent with the assigned structure and showed the product to be approximately 96% pure c isomer.

EXAMPLE 33

5-(2-Chlorobenzyloxy)-2-ethyl-5-methyl-1,3-dioxane

By the method of Example 32, 2-ethyl-5-hydroxymethyl-1,3-dioxane was reacted with 2-chlorobenzyl chloride to yield c-5-(2-chlorobenzyloxy)-r-2-ethyl-5-methyl-1,3-dioxane, b.p. 102°–104° C/0.0002 mm Hg, $n_D^{25}$ 1.5186. The ir and nmr spectra were consistent with the assigned structure and showed the product to be free of t-isomer. By gas chromatography the product was shown to be 96.5% pure.

EXAMPLE 34

5-Benzyloxy-2-(2-furyl)-1,3-dioxane

A. Preparation of 2-Benzyloxy-1,3-propanediol

A solution of 370 g of 5-benzyloxy-2-phenyl-1,3-dioxane and 35 ml of concentrated sulfuric acid in a medium of 750 ml of water and 1.2 l of ethanol was refluxed for 2 hours. The ethanol was then removed by evaporation under reduced pressure, and by-product benzaldehyde was removed by steam distillation. The aqueous mixture was saturated with potassium carbonate, and the product was extracted from the aqueous medium with ether. The ethereal solution was dried ($MgSO_4$) and evaporated under reduced pressure to give solid product, which upon recrystallization from a benzene/ligroine system gave 218 g of 2-benzyloxy-1,3-propanediol, m.p. 38°–39° C.

B. Preparation of 5-Benzyloxy-2-(2-furyl)-1,3-dioxane

A mixture of 18.2 g of 2-benzyloxy-1,3-propanediol (Example 34A), 9.6 g of furaldehyde and 4 g of Dowex 50W × 8 resin ($H^+$ form) in 100 ml of benzene was refluxed until the theoretical amount of water was formed (1.8 g). By-product water was removed as an azeotropic mixture which distilled from the reaction vessel during refluxing (2.2 ml collected). After the ionic resin was removed, the benzene solution was washed with two 50-ml portions of one percent ammonium hydroxide, dried with magnesium sulfate, filtered and evaporated under reduced pressure to give 13 g of an oil. The oil was vacuum distilled and those fractions boiling at 128°–130° C/$10^{-4}$ mm Hg($n_D^{25}$=1.5412 and $n_D^{25}$=1.5415) were collected as oils which crystallized to give a total of 6.0 g of 5-benzyloxy-2-(2-furyl)-1,3-dioxane, m.p. 50°–52° C.

Analysis: Calc'd for $C_{15}H_{16}O_4$: C 69.21; H 6.20; Found: C 69.44; H 6.00.

The nmr (nuclear magnetic resonance) spectrum of the product is shown in FIG. 14; it indicates that the product is a mixture of cis and trans isomers in a ratio of about 30:70; in the cis form there is a cis relationship between the

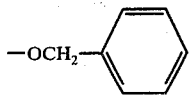

group and the furyl group.

EXAMPLE 35

Alternate Preparation of 5-Benzyloxy-2-(2-furyl)-1,3-dioxanes

A. 2-(2-Furyl)-5-hydroxy-1,3-dioxane

A mixture of 45 g of 2-furaldehyde, 43 g of glycerol and 2 g of Dowex 50W × 8 resin (Na+ form) in 100 ml of benzene was refluxed under a Dean-Stark trap for ca. 65 hours under a nitrogen atmosphere at the end of which time ca. 8 ml of water had collected. The reaction mixture was decanted from the resin, dried with magnesium sulfate, filtered and evaporated under reduced pressure to give 62 g of an oil. The oil was maintained at 40° C under an evacuated nitrogen atmosphere for 4 hours which reduced the oil to 58.7 g. The oil was then distilled and that fraction boiling at 80°–85° C/0.03–0.05 mm Hg was collected to give 43.5 g of 2-(2-furyl)-5-hydroxy-1,3-dioxane; $n_D^{25}$ 1.5017.

B. 5-Benzyloxy-2-(2-furyl)-1,3-dioxane

To a stirred solution of 17 g of 2-(2-furyl)-5-hydroxy-1,3-dioxane in 150 ml of toluene was added over a period of twenty minutes 4.4 g of sodium hydride (54.7% in mineral oil). The mixture was allowed to stir for 1 hour to permit evolution of by-product hydrogen, after which time 12.7 g of benzyl chloride was added during 15 minutes. The reaction mixture was heated to 70° C and maintained thereat for ca. 21 hours. The reaction mixture was allowed to cool to room temperature and remain at that temperature for 4 days. The mixture was washed with two 250-ml volumes of water, which aqueous washes were combined and extracted with toluene (three 150-ml volumes) to recover product. The toluene solution was combined with the washed reaction mixture and the total mixture was dried over magnesium sulfate, filtered and evaporated under reduced pressure to give 22.5 g of amber oil. The oil was washed with 25 ml of hexane, which procedure produced 17.5 g of clear oil. The clear oil was distilled and those fractions boiling at a bath temperature of 144°–154° C under 2 × 10$^{-4}$ mm Hg (bath temp. 144°–147°; $n_D^{25}$ 1.5349: bath temp. 148°–154°; $n_D^{25}$ 1.5379) were combined (10.6 g) and a portion was submitted for elemental analysis. Upon refrigeration for ca. 48 hours, 0.5 g of crystalline 5-benzyloxy-2-(2-furyl)-1,3-dioxane precipitated, m.p. 58.5°–61° C.

Analysis: Calc'd for $C_{15}H_{16}O_4$: C 69.21; H 6.20; Found: C 69.11; H 5.95.

EXAMPLE 36

5-(2-Fluorobenzyloxy)-2-(2-furyl)-1,3-dioxane

Using the procedure of Example 35B, 17 g of 2-(2-furyl)-5-hydroxy-1,3-dioxane was reacted with 4.4 g of sodium hydride, and then with 14.5 g of o-fluorobenzyl chloride in 150 ml of toluene. The reaction mixture was washed with water and the water washes extracted with toluene as described in Example 35B. The toluene extract was combined with the reaction mixture and the total mixture was washed with 150 ml of water. The reaction mixture was then dried, filtered and evaporated as in Example 35B to give 24.3 g of amber oil. The oil was washed with hexane to give 21.5 g of clear oil. The clear oil was distilled under reduced pressure and those fractions boiling at a bath temperature of 151.5°–160° C ($n_D^{25}$ 1.5219) and 161°–166° C ($n_D^{25}$ 1.5275) under 2 × 10$^{-4}$ mm Hg were collected. That fraction boiling at bath temperature 151.5°–160° was triturated with petroleum ether (b.p. 30°–60° C) to give crystalline product, and crystals therefrom were used to seed that fraction boiling at bath temperature of 161°–166° C. The crystalline products collected by filtration were combined to give 0.2 g of 5-(2-fluorobenzyloxy)-2-(2-furyl)-1,3-dioxane, m.p. 50.5°–52° C.

EXAMPLE 37

2-(2-Furyl)-5-(2-methylbenzyloxy)-1,3-dioxane

Using the procedure of Example 35B, 14 g of 2-(2-furyl)-5-hydroxy-1,3-dioxane was reacted with 3.6 g of sodium hydride and then with 15.2 g o-methylbenzyl bromide in 125 ml of toluene. The reaction mixture was washed with water as described in Example 35B, and the combined aqueous washes was extracted with two 150-ml volumes of toluene. The toluene extract was combined with the reaction mixture and the total mixture was washed with 100 ml of water, then dried, filtered and evaporated as in Example 35B to give 20.5 g of yellow oil. The oil was washed with hexane to give 17.8 g of amber oil which was distilled under reduced pressure. Those fractions distilling at a bath temperature of 152°–160° C ($n_D^{25}$ 1.5347) and 161.5°–165° C ($n_D^{25}$ 1.5385) under 2 × 10$^{-4}$ mm Hg were collected and refrigerated. That fraction boiling at a bath temperature of 152°–160° C crystallized, and was used to seed the fraction boiling at a bath temperature of 161.5°–165°. The crystalline product was removed by filtration to give 0.4 g of 2-(2-furyl)-5-(2-methylbenzyloxy)-1,3-dioxane, m.p. 64°–65° C.

EXAMPLE 38

Preparation of 5-Benzyloxy-2-chloromethyl-1,3-dioxane

A. 2-Benzyloxy-1,3-propanediol

A solution of 370 g of 5-benzyloxy-2-phenyl-1,3-dioxane and 35 ml of concentrated sulfuric acid in a medium of 750 ml of water and 1.2 l of ethanol was refluxed for 2 hours. The ethanol was then removed by evaporation under reduced pressure, and by-product benzaldehyde was removed by steam distillation. The aqueous mixture was saturated with potassium carbonate, and the product was extracted from the aqueous medium with ether. The ethereal solution was dried (MgSO$_4$) and evaporated under reduced pressure to give solid product, which upon recrystallization from a benzene/ligroine system gave 218 g of 2-benzyloxy-1,3-propanediol, m.p. 38°–39° C.

B. 5-Benzyloxy-2-chloromethyl-1,3-dioxane

A mixture of 5.0 g of 2-benzyloxy-1,3-propanediol, 3.5 g of chloroacetaldehyde dimethyl acetal and 0.3 g of p-toluenesulfonic acid was heated via oil bath through the temperature range 25° to 130° C in a three-necked, round-bottomed flask equipped with stirrer, thermometer and condenser. The by-product methanol, removed by distillation during the course of reaction, amounted to 63% of theory. The reaction mixture was cooled to room temperature and dissolved in ether. The ether solution was washed with 10% sodium carbonate and then with water. After drying over anhydrous sodium sulfate, the ether was removed under reduced pressure. Distillation of the crude oil gave 3.3 g of 5-benzyloxy-2-chloromethyl-1,3-dioxane; b.p. 100°–105° C/0.025 mm Hg; $n_D^{25}$ 1.5228. The nmr spectrum was consistent with the assigned structure and showed the cis isomer content to be 30 ± 5%, the remainder being the trans isomer.

Analysis: Calc'd. for $C_{12}H_{15}ClO_3$: C 59.38; H 6.23; Found: C 59.56; H 6.49.

The preparation was repeated and the isomeric mixture separated by column chromatography. The pure cis isomer was a solid, m.p. 38°–39° and the trans isomer was a liquid, $n_D^{23}$ 1.5200.

EXAMPLE 39

Preparation of 2-Chloromethyl-5-(2-fluorobenzyloxy)-5-methyl-1,3-dioxane

A. Diethyl 2-(2-fluorobenzyloxy)-2-methylmalonate

To a suspension of 20.2 g of sodium hydride in 1,200 ml of anhydrous toluene, in a 2-liter flask equipped with stirring bar, thermometer, dropping funnel and condenser with drying tube, was added 88.4 g of 2-fluorobenzyl alcohol. Addition was carried out at 25°–30° C during 45 minutes. The reaction mixture was heated at 90° C for 1½ hours. After the mixture was cooled, 177.1 g of diethyl 2-bromo-2-methylmalonate was added during 1¼ hours at 30°–50° C. The reaction mixture was heated at 90°–95° C for 2 hours. After remaining at room temperature overnight, the reaction mixture and 500 ml of ether were added to a vessel containing 1 liter of saturated sodium bicarbonate solution and 1 kg of crushed ice. After the ice had melted, the aqueous phase was separated and extracted with three 500-ml portions of ether. Ethereal solutions were combined, washed with three 500-ml portions of water and dried by filtration through sodium sulfate. Removal of ether and residual toluene (at reduced pressure) gave 176.2 g of diethyl 2-(2-fluorobenzyloxy)-2-methylmalonate, the identity of which was confirmed by its ir spectrum.

B. 2-(2-Fluorobenzyloxy)-2-methyl-1,3-propanediol

A dispersion of 19 g of lithium aluminium hydride in 600 ml of anhydrous ether was placed in a 1-liter flask equipped with stirrer, dropping funnel and condenser with drying tube. To this was added 74.6 g of diethyl 2-(2-fluorobenzyloxy)-2-methylmalonate at a rate sufficient to maintain refluxing. After addition, the reaction mixture was refluxed for 2 hours. The mixture was cooled and excess reducing agent was decomposed with a saturated sodium sulfate solution. Two hundred ml of ice-water and 1 liter of 10 percent sulfuric acid was added, and the resulting aqueous phase was saturated with sodium chloride and extracted with two 400-ml portions of ether. Ether solutions were combined, dried ($Na_2SO_4$) and concentrated to give an oil. Residual volatile materials were removed by distillation at 0.01 mm Hg to give solid which was recrystallized from petroleum ether-chloroform to give 17.8 g of 2-(2-fluorobenzyloxy)-2-methyl-1,3-propanediol; m.p. 72.5°–74.5° C. A small sample was recrystallized twice from carbon tetrachloride to give white needles, m.p. 75°–76°. The ir and nmr were consistent with the assigned structure.

Analysis: Calc'd for $C_{11}H_{15}FO_3$: C 61.66; H 7.06; Found: C 62.63, H 7.21.

C. 2-Chloromethyl-5-(2-fluorobenzyloxy)-5-methyl-1,3-dioxane

A mixture of 8.6 g of 2-(2-fluorobenzyloxy)-2-methyl-1,3-propanediol, 6.5 g chloroacetaldehyde diethyl acetal and 0.5 g of p-toluenesulfonic acid was heated in a 25 ml distillation flask; during the course of reaction 3.1 g of ethanol was removed by distillation. The warm residue was dissolved in 200 ml of benzene and the benzene solution was washed with two 50-ml portions of ten percent sodium carbonate and two 50-ml portions of water. The washed benzene solution was dried ($Na_2SO_4$) and concentrated at reduced pressure to give a brown liquid. Isomers were separated on a silica gel column (3.0:33 cm), following the progress of elution by thin layer chromatography. The isomeric mixture was applied to the column with a small amount of petroleum ether and 250 ml of high boiling (b.p. 65°–110° C) petroleum ether was passed through. Isomers were eluted with 99:1 petroleum ether-ethyl acetate, collecting 50 ml fractions (fractions 3 through 36). Fractions 16–20, after removal of solvent, gave a liquid which was distilled to give 3.45 g or r-2-chloromethyl-t-5-(2-fluorobenzyloxy)-5-methyl-1,3-dioxane; b.p. 96°–101° C/0.13 to $9 \times 10^{-4}$ mm Hg. After removal of solvent, fractions 22–36 gave a solid which was recrystallized from low boiling petroleum ether to give 5.3 g of r-2-chloromethyl-c-5-(2-fluorobenzyloxy)-5-methyl-1,3-dioxane, m.p. 42°–44° C. A sample of the solid product was recrystallized for elemental analysis.

Analysis: Calc'd for $C_{13}H_{16}FClO_3$: C 56.83; H 5.87; Found (t-isomer): C 56.69; H 5.97; Found (c-isomer): C 56.58; H 6.05.

EXAMPLE 40

5-Benzyloxy-2-bromomethyl-1,3-dioxane

By the method of Example 38, 2-benzyloxy-1,3-propanediol was reacted with bromoacetaldehyde diethyl acetal to yield 5-benzyloxy-2-bromomethyl-1,3-dioxane; b.p. 130°–133° C/$10^{-4}$ mm Hg; $n_D^{25}$ 1.5395. The nmr spectrum was consistent with the assigned structure and indicated the cis-isomer content was 30 ± 5%, the remainder being trans.

Analysis: Calc'd for $C_{12}H_{15}BrO_3$: C 50.19; H 5.27; Found: C 50.48; H 5.56.

EXAMPLE 41

5-Benzyloxy-2-bromomethyl-5-methyl-1,3-dioxane

By the method of Example 39, 2-benzyloxy-2-methyl-1,3-propanediol was reacted with bromoacetaldehyde diethyl acetal to yield an oil which was distilled at 133° to 135° C/0.022 mm Hg to give a mixture of cis- and trans- isomers. The mixture of isomers was separated by column chromatography on silica gel. t-5-Benzyloxy-r-2-bromomethyl-5-methyl-1,3-dioxane was purified by distillation; b.p. 116°–119° C/4.5 × $10^{-4}$ mm Hg, $n_D^{26}$ 1.5308. The c-isomer was purified by recrystallization from petroleum ether to give c-5-benzyloxy-r-2-bromoethyl-5-methyl-1,3-dioxane; m.p. 55°–56° C. The purity and stereochemistry of both isomers were determined by thin layer chromatography and nmr.

Analysis: Calc'd for $C_{13}H_{17}BrO_3$: C 51.84; H 5.69; Found (t-isomer): C 52.16; H 5.53; Found (c-isomer): C 52.06; H 5.59.

EXAMPLE 42

5-Benzyloxy-2-chloromethyl-5-methyl-1,3-dioxane

By the method of Example 39 2-benzyloxy-2-methyl-1,3-propanediol was reacted with chloroacetaldehyde dimethyl acetal to yield a mixture of isomers which was separated by column chromatography on silica gel. The t-isomer was purified by distillation to give t-5-benzyloxy-r-2-chloromethyl-5-methyl-1,3-dioxane, b.p. 88°–112° C/2 × 10$^{-4}$ mm Hg. The c-isomer was purified by recrystallization from pentane twice to give c-5-benzyloxy-r-2-chloromethyl-5-methyl-1,3-dioxane, m.p. 50°–51° C. Isomer structures were assigned on the basis of nmr studies.

Analysis: Calc'd for $C_{13}H_{17}ClO_3$: C 60.81; H 6.68; Found (t-isomer): C 60.73; H 6.78; Found (c-isomer): C 60.64; H 6.96.

EXAMPLE 43

2-Chloromethyl-b 5-(2-methylbenzyloxy)-1,3-dioxane

A mixture of 124 g chloroacetaldehyde dimethyl acetal, 92 g glycerol, and 1 g p-toluenesulfonic acid was placed in a flask equipped with a stirrer, condenser, Dean-Stark trap and thermometer. The mixture was heated to 80°–85° C until 76 ml of methanol had been removed and no additional methanol was distilling over. The solution was then cooled, neutralized with sodium carbonate, and extracted with ether. Removal of the ether under reduced pressure gave 151 g of light-yellow oil which was distilled to yield 108.5 g of 2-chloromethyl-5-hydroxy-1,3-dioxane, b.p. 78°–80° C/0.15 mm Hg, 17.1% cis-isomer.

2-Chloromethyl-5-hydroxy-1,3-dioxane (30.2 g) and 125 ml of toluene were placed in a flask equipped with a stirrer, condenser, thermometer, and addition funnel, and 8.6 g of 57% sodium hydride was added cautiously in small portions with agitation. After the addition was complete the slurry was stirred at room temperature for 30 minutes, and then 37.0 g of α-bromo-o-xylene was added dropwise. When this addition was complete the reaction mixture was heated and held at reflux temperature for three hours. The cooled reaction mixture was washed twice with 100-ml portions of water, and the organic layer was then dried over sodium sulfate. The solvent was removed under vacuum to yield 52 g of oil which was distilled to yield 33.1 g of material b.p. 128°–134° C/0.15 mm Hg. This distillate was redistilled with a spinning band column to yield 27.5 g of distillate, b.p. 102°–104° C/0.1 mm Hg; the pot residue crystallized on cooling, m.p. 58°–61° C. The pot residue recrystallized twice from benzene and ligroine yielded 2.2 g of 2-chloromethyl-5-(2-methylbenzyloxy)-1,3-dioxane, m.p. 62°–63° C, analyzing 98% cis-isomer by nmr spectroscopy. A portion recrystallized for analysis melted at 63°–63.5° C.

Analysis: Calc'd. for $C_{13}H_{17}ClO_3$: C 60.82; H 6.82; Found: C 60.84; H 6.66.

EXAMPLE 44

2-Chloromethyl-5-(2-fluorobenzyloxy)-1,3-dioxane

By the method of Example 43, 2-chloromethyl-5-hydroxy-1,3-dioxane was reacted with sodium hydride and o-fluorobenzyl chloride to yield 2-chloromethyl-5-(2-fluorobenzyloxy)-1,3-dioxane. This mixture of isomers was distilled using a short path distillation apparatus at 0.1 mm to obtain three fractions. Fraction 1, b.p. 95°–100°/0.1 mm was found by VPC analysis to be 3.8% cis-2-chloromethyl-5-(2-fluorobenzyloxy)-1,3-dioxane (the remainder in each case being the trans isomer). Fraction 2, b.p. 98°–102°/0.1 mm was 13.8% cis isomer. Fraction 3, b.p. 165°–170°/0.1 mm was 99% cis and solidified on standing; the solid was sublimed to a solid, m.p. 60°–62°, which was found by nmr analysis to 94% cis isomer and 6% trans isomer.

Analysis: Calc'd for $C_{12}H_{14}ClFO_3$: C 55.26; H 5.41; Found: C 55.35; H 5.19.

EXAMPLE 45

2-Chloromethyl-5-(2-methylbenzyloxy)-5-methyl-1,3-dioxane

By the method of Example 39, 2-(2-methylbenzyloxy)-2-methyl-1,3-propanediol was reacted with chloroacetaldehyde diethyl acetal to yield a mixture which was separated by column chromatography. The t-isomer was a liquid b.p. 117° C/0.005 mm Hg; $n_D^{25}$ 1.5175. The c-isomer was a solid, m.p. 57°–58° C.

Analysis: Calc'd for $C_{14}H_{19}ClO_3$: C 62.11; H 7.07; Found (t-isomer): C 62.32; H 7.34; Found (c-isomer): C 62.12; H 7.12.

EXAMPLE 46

2-Chloromethyl-5-(2-chlorobenzyloxy)-5-methyl-1,3-dioxane

By the method of Example 39, 2-(2-chlorobenzyloxy)-2-methyl-1,3-propanediol was reacted with chloroacetaldehyde diethyl acetal to yield a mixture of isomers which were separated by column chromatography. The cis-isomer was a solid, m.p. 53°–54° C. The trans-isomer was a liquid, b.p. 104°–107° C/0.02 mm Hg; $n_D^{25}$ 1.5280.

Analysis: Calc'd for $C_{13}H_{16}Cl_2O_3$: C 53.63; H 5.54; Found (cis-isomer): C 53.85; H 5.49; Found (trans-isomer): C 53.89; H 5.39.

EXAMPLE 47

5-(2-Fluorobenzyloxy)-2-(methoxymethyl)-5-methyl-1,3-dioxane

In a 25 ml round-bottomed flask equipped with stirrer and a short path distillation apparatus were placed 10.0g of 2-(2-fluorobenzyloxy)-2-methyl-1,3-propanediol prepared as in Example 31, 7.69 g of methoxyacetaldehyde diethyl acetal and 0.5 g of p-toluenesulfonic acid. The mixture was heated until ethanol evolution ceased (4.1 g collected of 4.3 g theoretical). The contents of the flask were dissolved in 200 ml of benzene, the solution was washed with aqueous sodium carbonate, dried over sodium sulfate and concentrated under reduced pressure to give 12.7 g of a mixture of isomers. The isomers were separated by passage through a silica gel column using mixtures of petroleum ether and ethyl acetate (initially pure petroleum ether, then with added ethyl acetate to finally 90:10 ratio) as eluting solvent and thin layer chromatography to follow the appearance of the isomers.

The first fractions were combined and concentrated to give 5.2 g of t-5-(2-fluorobenzyloxy)-r-2-methoxymethyl-5-methyl-1,3-dioxane, b.p. 151°–152°/1.5 mm; $n_D^{25}$ 1.4920.

The later fractions were combined and concentrated to give 3.0 g of c-5-(2-fluorobenzyloxy)-r-2-methoxymethyl-5-methyl-1,3-dioxane, m.p. 31°–32°. The ir and nmr spectra of the two products were consistent with the assigned structures.

Analysis: Calc'd for $C_{14}H_{19}FO_4$: C 62.21; H 7.09; Found for t-isomer: C 62.44; H 6.85; Found for c-isomer: C 62.25; H 6.85.

EXAMPLE 48

2-(2-Chloroethyl)-5-(2-fluorobenzyloxy)-5-methyl-1,3-dioxane

According to the procedure of Example 47, 8.5 g of chloroacetaldehyde diethyl acetal and 11.0 g of 2-(2-fluorobenzyloxy)-2-methyl-1,3-propanediol were reacted in the presence of 0.02 g of p-toluenesulfonic acid to give, after separation by column chromatography, 5.1 g of t-2-(2-chloroethyl)-r-5-(2-fluorobenzyloxy)-5-methyl-1,3-dioxane, b.p. 130°/0.005 mm, $n_D^{25}$ 1.5026; and 4.3 g of c-2-(2-chloroethyl)-r-5-(2-fluorobenzyloxy)-5-methyl-1,3-dioxane, b.p. 120°/0.01 mm; $n_D^{25}$ 1.5050. The ir and nmr spectra were consistent with the assigned structures.

EXAMPLE 49

5-Benzyloxy-2-benzyloxymethyl-1,3-dioxane

Using the procedure of Example 47, benzyloxyacetaldehyde diethyl acetal and 2-benzyloxy-1,3-propanediol were reacted to give 5-benzyloxy-2-benzyloxymethyl-1,3-dioxane, $n_D^{25}$ 1.5438. The ir spectrum was consistent with the assigned structure. The nmr spectrum indicated 28% cis isomer and 72% trans isomer.

EXAMPLE 50

5-Benzyloxy-2-(3-chlorophenoxymethyl)-1,3-dioxane

Using the procedure of Example 47, (3-chlorophenoxy)acetaldehyde diethyl acetal and 2-benzyloxy-1,3-propanediol were reacted to give 5-benzyloxy-2-(3-chlorophenoxymethyl)-1,3-dioxane, $n_D^{25}$ 1.5587. The ir spectrum was consistent with the assigned structure. The nmr spectrum indicated 40% cis isomer and 60% trans isomer.

EXAMPLE 51

5-Benzyloxy-2-methyl-2-phenyl-1,3-dioxane

A mixture of 18.2 g of 2-benzyloxy-1,3-propanediol, 12.1 g of acetophenene and 0.1 g of p-toluenesulfonic acid in 75 ml of benzene and 75 ml of toluene was heated under a Dean-Stark apparatus until 2.0 ml of water had been collected. The mixture was washed twice with 75 ml of 5% aqueous sodium bicarbonate, then with water. After drying over magnesium sulfate, the solution was concentrated under reduced pressure to give 1.6 g of oil which crystallized on standing to give a solid, m.p. 76°-79° C. Recrystallization gave 5-benzyloxy-2-methyl-2-phenyl-1,3-dioxane, m.p. 87°-88°. The ir and nmr spectra were consistent with the assigned structure. The nmr spectrum indicated 50% cis isomer and 50% trans isomer.

EXAMPLE 52

5-(2-Fluorobenzyloxy)-2,5-dimethyl-1,3-dioxane

Using the procedure of Example 51, 2-(2-fluorobenzyloxy)-2-methyl-1,3-propanediol and acetaldehyde were reacted, using hexane as solvent to give, after separation by column chromatography, t-5-(2-fluorobenzyloxy)-r-2-methyl-5-methyl-1,3-dioxane, $n_D^{25}$ 1.4902, and c-5-(2-fluorobenzyloxy)-r-2-methyl-5-methyl-1,3-dioxane, $n_D^{25}$ 1.4939. The ir and nmr spectra were consistent with the assigned structures.

EXAMPLE 53

5-(2-Fluorobenzyloxy)-2-(3-fluorophenyl)-5-methyl-1,3-dioxane

Using the procedure of Example 51, 3-fluorobenzaldehyde and 2-(2-fluorobenzyloxy)-2-methyl-propanediol were reacted, using benzene as solvent, to give, after separation by column chromatography, c-5-(2-fluorobenzyloxy)-r-2-(3-fluorophenyl)-5-methyl1,3-dioxane, m.p. 86°-87°, and t-5-(2-fluorobenzyloxy)-r-2-(3-fluorophenyl)-5-methyl-1,3-dioxane, m.p. 83°-84°.

EXAMPLE 54

5-(2-Fluorobenzyloxy)-5-methyl-2-thienyl-1,3-dioxane

Using the procedure of Example 51, thiophene-2-carboxaldehyde and 2-(2-fluorobenzyloxy)-2-methyl-1,3-propanediol were reacted, using benzene as solvent, to give, after separation by column chromatograph, c-5-(2-fluorobenzyloxy)-5-methyl-r-2-thienyl-1,3-dioxane, m.p. 111°-112°, and t-5-(2-fluorobenzyloxy)-5-methyl-r-2-thienyl-1,3-dioxane, m.p. 84°-85°.

EXAMPLE 55

3-Benzyloxy-1,5-dioxaspiro[5.5]undecane

Using the procedure of Example 51, cyclohexanone and 2benzyloxy-1,3-propanediol were reacted, using benzene as solvent, to give after distillation, 3-benzyloxy-1,5-dioxaspiro[5.5]undecane, b.p. 120°-121°/0.05 mm. The ir spectrum was consistent with the assigned structure.

EXAMPLE 56

2-Phenyl-5-(2-pyridyl)methoxy-1,3-dioxane

A solution of cis-5-hydroxy-2-phenyl-1,3-dioxane in 300 ml of benzene was treated with 4.45 g of 54% sodium hydride and the mixture stirred at ambient temperature until gas evolution ceased. To this mixture was added a solution of 2-chloromethylpyridine (obtained by extracting with benzene a carefully neutralized solution of 18.04 g of 2-chloromethylpyridine hydrochloride in 50 ml of water, then drying the benzene extracts) and the mixture was heated under reflux for 19 hours. The mixture was filtered and the filtrate washed with water and dried over sodium sulfate. Removal of the benzene under reduced pressure gave yellow solid which on recrystallization from benzene-petroleum ether (65°-110°) gave 14.2 g of cis-2-phenyl-5-(2-pyridyl)methoxy-1,3-dioxane, m.p. 95°-98°. The nmr spectrum was consistent with the assigned structure and indicated pure cis isomer.

EXAMPLE 57

2-Phenyl-5-(2-thienyl)methoxy-1,3-dioxane

Using the procedure of Example 56, cis-5-hydroxy-2-phenyl-1,3-dioxane was reacted with 2-chloromethylthiophene to give, after repeated recrystallization from petroleum ether, cis-2-phenyl-5-(2-thienyl)methoxy-1,3-dioxane m.p. 68.5°-69°. The ir and nmr spectra were consistent with the assigned structure.

EXAMPLE 58

5-(2-Fluorobenzyloxy)-2-(2-furyl)-5-methyl-1,3-dioxane

Using the procedure of Example 51, freshly distilled furfural and 2-benzyloxy-2-methyl-1,3-propanediol were reacted, using benzene as solvent, to give, after separation by column chromatography and recrystallization of the two isomers from petroleum ether t-5-(2-fluorobenzyloxy)-r-2-(2-furyl)-5-methyl-1,3-dioxane, m.p. 67.5°-69°, and c-5-(2-fluorobenzyloxy)-r-2-(2-furyl)-5-methyl-1,3-dioxane, m.p. 92.5°-94.5°.

EXAMPLE 59

5-Bromomethyl-2-ethyl-5-(2-methylbenzyloxy)-1,3-dioxane

A mixture of 5.0 g of 6-ethyl-1,5,7-trioxaspiro[2.5]octane, prepared as in Example 32B, and 9.63 g of 2-methylbenzyl bromide in 40 ml of dimethylformamide was heated under reflux for 5 hours. The mixture was poured into 300 ml of ice water and stirred for 300 minutes, then extracted with diethyl ether. The ether extracts were washed with water, dried over sodium sulfate and concentrated under reduced pressure to give 3.3 g of yellow oil. Thin-layer chromatographic analysis indicated five components. The yellow oil was stirred with 3 g of silica gel and this coated silica gel placed on top of a column previously packed with 27 g of silica gel. Elution was carried out using high-boiling (65°-110°) petroleum ether as the elution solvent and collecting 50 ml fractions. The progress of separation was followed by thin-layer chromatography. The third component eluted (fractions 14-17) had the nmr spectrum anticipated for the desired product. The solid remaining after fractions 14-17 were combined and concentrated was recrystallized from petroleum ether (65°-110°) to give 0.4 g of 5-bromomethyl-r-2-ethyl-c-5-(2-methylbenzyloxy)-1,3-dioxane, m.p. 77°-79°.

Analysis: Calc'd for $C_{15}H_{21}BrO_3$: C 54.72; H 6.43; Br, 24.27; Found: 54.99; 6.46; 24.26.

EXAMPLE 60

5-Benzyloxy-2,2-dimethyl-1,3-dioxane

Using the procedure of Example 51, 2-benzyloxy-1,3-propanediol and acetone were reacted, using benzene as solvent, to give, after distillation using a short path column, 5-benzyloxy-2,2-dimethyl-1,3-dioxane. The nmr spectrum was consistent with the assigned structure.

EXAMPLE 61

2-Butyl-5-(2-fluorobenzyloxy)-5-methyl-1,3-dioxane

Using the procedure of Example 51, 2-(2-fluorobenzyloxy)-2-methyl-1,3-propanediol and valeraldehyde were reacted, using benzene as solvent, to give, after separation by column chromatography, r-2-butyl-t-5-(2-fluorobenzyloxy)-5-methyl-1,3-dioxane, b.p. 105°/0.05 mm, $n_D^{25}$ 1.4840; and r-2-butyl-c-5-(2-fluorobenzyloxy)-5-methyl-1,3-dioxane, b.p. 105°/0.025 mm, $n_D^{25}$ 1.4865. The ir and nmr spectra were consistent with the assigned structures.

Analysis: Calc'd. for $C_{16}H_{23}FO_3$: C 68.06; H 8.21; Found for t-isomer: C 68.27; H 8.31; Found for c-isomer: C 68.14; H 8.02.

EXAMPLE 62

2-(tert-Butyl)-5-(2-fluorobenzyloxy)-5-methyl-1,3-dioxane

Using the procedure of Example 51, 2-(2-fluorobenzyloxy)-2-methyl-1,3-propanediol and 2,2-dimethylpropanal were reacted, using benzene as solvent, to give, after separation by column chromatography, r-2-(tert-butyl)-t-5-(2-fluorobenzyloxy)-5-methyl-1,3-dioxane, m.p. 50°-52°; and r-2-(tert-butyl)-C-5-(2-fluorobenzyloxy)-5-methyl-1,3-dioxane, m.p. 85°-87°. The ir and nmr spectra were consistent with the assigned structures.

Analysis: Calc'd. for $C_{16}H_{23}FO_3$: C 68.06; H 8.21; Found for t-isomer: C 68.33; H 8.01; Found for c-isomer: C 67.97; H 8.38.

EXAMPLE 63

3-(2-Fluorobenzyloxy)-3-methyl-1,5-dioxaspiro[5.5]undecane

Using the procedure of Example 51, cyclohexanone and 2-(2-fluorobenzyloxy)-2-methyl-1,3-propanediol were reacted, using benzene as solvent, to give 3-(2-fluorobenzyloxy)-3-methyl-1,5-dioxaspiro[5.5]undecane, b.p. 170°-174°/0.03 mm, $n_D^{25}$ 1.5081. The ir and nmr spectra were consistent with the assigned structure.

Analysis: Calc'd for $C_{17}H_{23}FO_3$: C 69.37; H 7.88; Found C 69.59; H 7.93.

EXAMPLE 64

2,5-Diethyl-5-(2-fluorobenzyloxy)-1,3-dioxane

Using the procedure of Example 51, propionaldehyde and 2-ethyl-2-(2-fluorobenzyloxy)-1,3-propanediol were reacted, using hexane as solvent, to give, after separation by column chromatography, r-2-ethyl-5-ethyl-t-5-(2-fluorobenzyloxy)-1,3-dioxane, b.p. 89°-90°/0.01 mm, $n_D^{26}$ 1.4895; and r-2-ethyl-5-ethyl-c-5-(2-fluorobenzyloxy)-1,3-dioxane, b.p. 93°-95°/0.01 mm, $n_D^{26}$ 1.4902. The ir and nmr spectra were consistent with the assigned structures.

Analysis: Calc'd for $C_{15}H_{21}FO_3$: C 67.14; H 7.89; Found for t-isomer: C 67.05; H 7.77; Found for c-isomer: C 66.91; H 7.62.

EXAMPLE 65

5-Butyl-2-ethyl-5-(2-fluorobenzyloxy)-1,3-dioxane

Diethyl 2-butyl-2-(2-fluorobenzyloxy)malonate was prepared by reaction of 2-fluorobenzyl alcohol with diethyl 2-bromo-2-butylmalonate and the crude ester was reduced, without purification, with lithium aluminum hydride, all according to the method of Example 31, part A, to give 2-butyl-2-(2-fluorobenzyloxy)-1,3-propanediol, b.p. 140°-150°/0.01 mm, $n_D^{25}$ 1.5555, m.p. 66°-67°.

Reaction of this propanediol with propionaldehyde according to the procedure of Example 51, using hexane as solvent, gave, after separation by column chromatography, 5-butyl-r-2-ethyl-5-t-(2-fluorobenzyloxy)-1,3-dioxane, b.p. 107°-110°/0.02 mm, $n_D^{25}$ 1.4855, and 5-butyl-r-2-ethyl-c-5-(2-fluorobenzyloxy)-1,3-dioxane, b.p. 122°/0.025 mm, $n_D^{25}$ 1.4860.

Analysis: Calc'd for $C_{17}H_{25}FO_3$: C 68.89; H 8.50; Found for t-isomer: C 69.14; H 8.44; Found for c-isomer: C 68.32; H 8.20.

EXAMPLE 66

5-Benzyloxy-5-methyl-2-phenyl-1,3-dioxane

A. Preparation of 2-Benzyloxy-2-methyl-1,3-propanediol

A mixture of 236.3 g 3,4-dihydropyran and 90.1 g 1,3-dihydroxy-2-propanone, to which had been added 20 drops of concentrated hydrochloric acid, was heated to 85° C at which temperature, an exothermic reaction began. A cooling bath was applied to maintain the temperature in the range 85°-95° C during the next 15 minutes when heat was again applied to maintain the temperature at 85°–95° C for 2 hours. Excess dihydropyran was removed by warming under reduced pressure and the residue was dissolved in 600 ml of diethyl ether. The ether solution was washed (4 × 200 ml) with 5% aqueous sodium carbonate, then with water (3 × 300 ml) and dried over magnesium sulfate. The dried solution was distilled under reduced pressure to give 172.7 g of 1,3-bis(2-tetrahydropyranyloxy)-2-propanone, b.p. 90°–97°/2 × $10^{-4}$ mm.

A solution of 0.14 moles of methylmagnesium bromide in diethyl ether was prepared by dissolving 15.5 g of 3M methylmagnesium bromide solution (in diethyl ether) in 100 ml of specially dried diethyl ether. While stirring at 25°–30°, a solution of 25.8 g of 1,3-bis(2-tetrahydropyranyloxy)-2-propanone, prepared as above, in 100 ml of diethyl ether was added dropwise. A white solid separated and refluxing occurred. The mixture was warmed to maintain reflux for 1 hour, then allowed to stand for 16 hours. Saturated ammonium chloride solution (100 ml) was added very slowly and when addition was completed, the layers were separated. The aqueous layer was extracted (2 × 100 ml) with diethyl ether. The ether solutions were combined, washed (2 × 100 ml) with water and dried over magnesium sulfate. The dried solution was concentrated and distilled to give 16.2 g of 2-methyl-1,3-bis(2-tetrahydropyranyloxy)-2-propanol, b.p. 121°–136°/2—3 × $10^{-4}$ mm.

A suspension of 3.1 g of sodium hydride in 100 ml of dimethylformamide was prepared and to it was added dropwise, during 0.5 hours, a solution of 27.4 g of 2-methyl-1,3-bis(2-tetrahydropyranyloxy)-2-propanol in 100 ml of dimethylformamide. Stirring was continued 1.8 hours after which a solution of 16.5 g of benzyl chloride in dimethylformamide was added dropwise during 0.5 hours. A slightly exothermic reaction occurred during the addition. The mixture was heated under reflux for 26 hours, then allowed to stand for 40 hours. The precipitated solid was removed by filtration and the dimethylformamide removed by distillation under reduced pressure. The residue was dissolved in 400 ml of diethyl ether, the solution was washed with water (3 × 150 ml) and dried over magnesium sulfate. The solvent was removed to five 32.6 g of yellow oil.

The yellow oil was mixed with 300 ml of acetic acid and the mixture heated under reflux for 25 hours. Excess acetic acid was removed by distillation under reduced pressure and the residue dissolved in 300 ml of diethyl ether. The solution was washed (2 × 60 ml) with 5% aqueous sodium carbonate, then with water (3 × 100 ml). The solution was dried and concentrated to give 35.1 g of crude 2-benzyloxy-2-methyl-1,3-propanediyl diacetate. The ir and nmr spectra confirmed the assigned structure.

The crude diacetate (35.1 g) was mixed with 475 ml of 10% aqueous sodium hydroxide and 475 ml of ethanol and the mixture heated under reflux for 3.4 hours, then allowed to stand for about 16 hours. The mixture was concentrated to about 400 ml, cooled and extracted with diethyl ether (3 × 275 ml). The extracts were combined, dried over magnesium sulfate and concentrated to give 21.4 g of an oil which crystallized to give 9.6 g of a brown solid. Repeated sublimation gave 6.8 g of white solid, m.p. 82°–83.5° which nmr indicated to contain a trace of mineral oil. Recrystallization from benzene gave 2-benzyloxy-2-methyl-1,3-propanediol, m.p. 89.5°–90°, which nmr spectra indicated to be free of hydrocarbon contamination.

Analysis: Calc'd for $C_{11}H_{16}O_3$: C 67.32; H 8.22; Found: C 66.85; H 7.50.

This diol was also conveniently prepared by reaction of benzyl alcohol with diethyl 2-bromo-2-methylmalonate and reduction of the 2-benzyloxy-2-methylmalonate thus produced to the desired diol.

B. Preparation of 5-Benzyloxy-5-methyl-2-phenyl-1,3-dioxane

A mixture of 4.5 g of 2-benzyloxy-2-methyl-1,3-propanediol, 2.5 g of benzaldehyde and 0.25 ml of 40% sulfuric acid in 100 ml of benzene was heated at reflux temperature under a Dean-Starks apparatus. After 0.5 hours, 0.6 ml of water had been collected and no more had collected at 0.8 hours. One ml of saturated aqueous potassium carbonate was added, then excess magnesium sulfate was added to dry the solution. The solution was concentrated under reduced pressure to give 6.0 g of a brown oil which was distilled to give 4.9 g of heavy oil. Redistillation gave 3.6 g of 5-benzyloxy-5-methyl-2-phenyl-1,3-dioxane, b.p. 133°–134° C/5 × $10^{-5}$ mm, $n_D^{25}$ 1.5515. The assigned structure was confirmed by ir and nmr spectra.

Analysis: Calc'd for $C_{18}H_{20}O_3$: C 76.03; H 7.09; Found: C 75.85; H 6.79.

A second sample was prepared using the method of Example 39C with 5.2 g of benzaldehyde, 9.5 g of 2-benzyloxy-2-methyl-1,3-propanediol and 300 ml of benzene containing a few crystals of p-toluenesulfonic acid. From the mixture was obtained 13.2 g of white oil which was found by nmr spectral analysis to be the expected mixture of two isomers.

A solution of 11.6 g of the mixture in 20 ml of petroleum ether (65°–110°) and 4 ml of ethyl acetate was subjected to separation on a 3 × 27 cm column of neutral silica gel. Elution was accomplished using petroleum ether (90)-ethyl acetate (10) as solvent. The first 400 ml of eluted material contained nothing. A second 400 ml of eluate was concentrated to obtain 6.8 g of white solid, m.p. 60°–62°. The third fraction (220 ml) yielded 0.2 g. The fourth fraction (100 ml) yielded 0.8 g white solid, m.p. 56°–57.5°. The fifth fraction (450 ml) yielded 3.2 g, m.p. 57°–58° and the sixth fraction (250 ml) yielded 0.3 g, m.p. 55°–56.5°.

Recrystallization of the solid from the second fraction using methanol-water gave a white solid, m.p. 64°–65° C, which was found by nmr spectral analysis to be pure t-5-benzyloxy-5-methyl-r-2-phenyl-1,3-dioxane.

Two recrystallizations of the combined solids from the second-sixth fractions gave white solid, m.p. 58°–59° C, which was found by nmr spectral analysis to be pure c-5-benzyloxy-5-methyl-r-2-phenyl-1,3-dioxane.

Analysis: Calc'd for $C_{18}H_{20}O_3$: C 76.03; H 7.09; Found: t-isomer: C 75.92; H 7.27; c-isomer: C 76.23; H 7.01.

EXAMPLE 67 c-5-(2-Fluorobenzyloxy)-r-2-(2-cyanoethyl)-5-methyl-1,3-dioxane

To a mixture of 2.9 g of r-2-(2-chloroethyl)-c-5-(2-fluorobenzyloxy)-5-methyl-1,3-dioxane and 0.76 g of sodium cyanide in 2.9 ml of deionized water was added 0.076 g of tributyl(hexadecyl)phosphonium bromide and the mixture was heated rapidly to the reflux temperature at which it was maintained for 4 hours. The mixture was cooled and extracted with 75 ml of diethyl ether. The ether extract was washed (3 × 25 ml) with water, dried with magnesium sulfate and concentrated to give 2.8 g of yellow oil. The yellow oil was distilled to give 2.4 g of c-5-(2-fluorobenzyloxy)-r-2-(2-cyanoethyl)-5-methyl-1,3-dioxane, b.p. 132°/0.01 mm, $n_D^{25}$ 1.5015. The ir and nmr spectra were consistent with the assigned structure.

Analysis: Calc'd for $C_{15}H_{18}FNO_3$: C 64.50; H 6.50; N 5.01; Found: C 64.48; H 6.37; N 4.77.

Using the same procedure, r-2-(2-chloroethyl)-t-5-(2-fluorobenzyloxy)-5-methyl-1,3-dioxane was reacted with sodium cyanide in water in the presence of tributyl(hexadecyl)phosphonium bromide to give r-2-(2-cyanoethyl)-t-5-(2-fluorobenzyloxy)-5-methyl-1,3-dioxane, b.p. 133°/0.01 mm.

Analysis: Calc'd for $C_{15}H_{18}FNO_3$: C 64.50; H 6.50; N 5.01; Found: C 64.63; H 6.57; N 4.74.

EXAMPLE 68

In similar manner to the above, may be prepared:
5-benzyl-2-ethyl-5-(2-fluorobenzyloxy)-1,3-dioxane; 5-(2-fluorobenzyloxy)-2-phenyl-5-methyl-1,3-dioxane; 5-(2-fluorobenzyloxy)-2-hexyl-5-methyl-1,3-dioxane; 5-(2-fluorobenzyloxy)-5-methyl-2-nonyl-1,3-dioxane; 2-cyclopropyl-5-(2-fluorobenzyloxy)-5-methyl-1,3-dioxane; 2-cyclohexyl-5-methyl-5-(2-methylbenzyloxy)-1,3-dioxane; 5-benzyloxy-5-chloromethyl-2-cyclopropyl-1,3-dioxane; 2-benzyl-5-(2-fluorobenzyloxy)-5-methyl-1,3-dioxane; 2-(2-chlorobenzyloxy)-5-ethyl-5-(2-phenylethyl)-1,3-dioxane; 2-(4-chlorophenoxymethyl)-5-(2-fluorobenzyloxy)-5-methyl-1,3-dioxane; 5-(2-fluorobenzyloxy)-5-methyl-2-propenyl-1,3-dioxane; 5-benzyloxy-2-methallyl-5-methyl-1,3-dioxane; 5-(2-chlorobenzyloxy)-5-methyl-2-vinyl-1,3-dioxane; 5-benzyloxy-5-methyl-2-(1-propynyl)-1,3-dioxane; 5-benzyloxy-5-cyanonethyl-2-(3-pluorophenyl)-1,3-dioxane, 5-(2-fluorophenyl)-5-(2-cyanoethyl)-2-ethyl-1,3-dioxane; 5-(2-fluorobenzyloxy)-5-methyl-2-(2-phenylvinyl)-1,3-dioxane; 5-benzyloxy-2-(2-(2-furyl)ethyl)-5-methyl-1,3-dioxane; 5-(2-fluorobenzyloxy)-5-methyl-(2-(2-thienylmethyl)-1,3-dioxane; 5-methyl-5-(2-methylbenzyloxy)-2-(methylthiomethyl)-1,3-dioxane; 5-benzyloxy-5-methyl-2-(methylsulfonylethyl)-1,3-dioxane; 2-(ethylsulfinylmethyl)-5-(2-fluorobenzyloxy)-5-methyl-1,3-dioxane; and 2-ethyl-5-(2-furylmethoxy)-5-methyl-1,3-dioxane.

EXAMPLE 69

Pre-emergence Herbicidal Activity of Substituted 5-Benzyloxy-1,3-dioxanes

Employing the general method of Example 1, the pre-emergence herbicidal activity of the substituted 5-benzyloxy-1,3-dioxanes was assessed. The results obtained are presented in Table 7.

Table 7

| Compound of Example | Species | Preemergence Herbicidal Activity of Substituted 5-Benzoyloxy-1,3-dioxanes (response at indicated rate) | | | | | | | |
|---|---|---|---|---|---|---|---|---|---|
| | | Rates in Pounds per Acre | | | | | | | |
| | | 8.0 | 6.0 | 4.0 | 3.0 | 2.0 | 1.5 | 1.0 | 0.75 |
| 27* | Corn | | 100 | | 100 | | 80[b] | | 0[b] |
| | Barnyard grass | | 95[a] | | 40[b] | | 40[b] | | 30[b] |
| | Crabgrass | | 100 | | 100 | | 100 | | 80[b] |
| | Mustard | | 30[b] | | 0[b] | | 0[b] | | 0 |
| | Chickweed | | 100 | | 80[b] | | 90[b] | | 50[b] |
| 28* | Corn | 100 | | 100 | | 100 | | 100 | |
| | Mustard | 0[a] | | 0[a] | | 0[b] | | 0 | |
| | Crabgrass | 100 | | 100 | | 95[1] | | 95[a] | |
| | Barnyard grass | 100 | | 100 | | 95[a] | | 40[b] | |
| | Cotton | 0 | | 0 | | 0 | | 0 | |
| 29* | Corn | 100 | | 100 | | 100 | | 20[a] | |
| | Mustard | 0[a] | | 0[b] | | 0[b] | | 0 | |
| | Crabgrass | 100 | | 100 | | 100 | | 100 | |
| | Barnyard grass | 100 | | 100 | | 100 | | 100 | |
| | Cottton | 0 | | 0 | | 0 | | 0 | |
| 30* | Corn | 100 | | 100 | | 100 | | 40[a] | |
| | Mustard | 10[a] | | 0[a] | | 0[b] | | 0[b] | |
| | Crabgrass | 100 | | 100 | | 100 | | 100 | |
| | Barnyard grass | 100 | | 100 | | 100 | | 90[a] | |
| | Cotton | 0 | | 0 | | 0 | | 0 | |
| 31 (c isomer) | Lima bean | 100 | | 75[b] | | 0[b] | | 0 | |
| | Corn | 100 | | 100 | | 100 | | 100 | |
| | Lettuce | 0[b] | | 0[b] | | 0[b] | | 0[b] | |
| | Mustard | 0[b] | | 0[b] | | 0[b] | | 0[b] | |
| | Crabgrass | 100 | | 100 | | 100 | | 100 | |
| 31 (t isomer) | Lima bean | 0 | | 0 | | 0 | | 0 | |
| | Corn | 0[b] | | 0 | | 0 | | 0 | |
| | Lettuce | 0 | | 0 | | 0 | | 0 | |
| | Mustard | 0[b] | | 0 | | 0 | | 0 | |
| | Crabgrass | 30[b] | | 10[b] | | 0[b] | | 0 | |
| 32 | Lima bean | 100 | | 75[a] | | 100 | | 0[b] | |
| | Corn | 100 | | 100 | | 70[a] | | 100 | |
| | Lettuce | 0[b] | | 0[b] | | 0[b] | | 0 | |
| | Mustard | 0[b] | | 0[b] | | 0[b] | | 0[b] | |
| | Crabgrass | 100 | | 100 | | 100 | | 100 | |
| 33 | Lima bean | 100 | | 0[b] | | 0[b] | | — | |
| | Corn | 100 | | 100 | | 100 | | 100 | |
| | Lettuce | 40[b] | | 0[b] | | 0[b] | 0[b] | | |
| | Mustard | 30[b] | | 0[b] | | 0[b] | | 0[b] | |
| | Crabgrass | 100 | | 100 | | 100 | | 100 | |
| 34 (pure cis isomer) | Corn | | | 100 | | 100 | | 30[a] | |
| | Mustard | | | 0[b] | | 0[b] | | 0 | |
| | Crabgrass | | | 100 | | 100 | | 100 | |
| | cotton | | | 0 | | 0 | | 0 | |
| | Barnyard grass | | | 100 | | 100 | | 80[a] | |
| | Soybeans | | | 0[a] | | 0[b] | | 0 | |
| 36** | Corn | 100 | | 100 | | 70[b] | | 0[b] | |
| | Mustard | 50[a] | | 0[b] | | 0[b] | | 0 | |
| | Crabgrass | 100 | | 100 | | 100 | | 100 | |
| | Barnyard grass | 100 | | 100 | | 100 | | 20[a] | |

Table 7-continued

Preemergence Herbicidal Activity of Substituted 5-Benzoyloxy-1,3-dioxanes (response at indicated rate)

| Compound of Example | Species | Rates in Pounds per Acre | | | | | | | |
|---|---|---|---|---|---|---|---|---|---|
| | | 8.0 | 6.0 | 4.0 | 3.0 | 2.0 | 1.5 | 1.0 | 0.75 |
| | Cotton | 100 | | $0^b$ | | 0 | | 0 | |
| | Soybeans | $30^a$ | | $0^b$ | | 0 | | 0 | |
| 37** | Corn | 100 | | $70^a$ | | $30^a$ | | $0^b$ | |
| | Mustard | $60^b$ | | $0^b$ | | $0^b$ | | 0 | |
| | Crabgrass | 100 | | 100 | | 100 | | $50^a$ | |
| | Barnyard grass | 100 | | $90^a$ | | $50^a$ | | $30^a$ | |
| | Cotton | $70^b$ | | $0^b$ | | 0 | | 0 | |
| | Soybeans | $0^a$ | | $0^b$ | | 0 | | 0 | |
| 38* | Corn | 100 | | 100 | | 100 | | 100 | |
| | Mustard | $0^a$ | | $0^b$ | | $0^b$ | | 0 | |
| | Crabgrass | 100 | | 100 | | 100 | | 100 | |
| | Barnyard grass | 100 | | $90^a$ | | 100 | | $50^a$ | |
| | Cotton | 0 | | 0 | | 0 | | 0 | |
| 39 | Lima bean | 100 | | $75^b$ | | $0^b$ | | 0 | |
| (c isomer) | Corn | 100 | | 100 | | 100 | | 100 | |
| | Lettuce | $0^b$ | | $0^b$ | | 0 | | 0 | |
| | Mustard | $0^b$ | | $0^b$ | | $0^b$ | | $0^b$ | |
| | Crabgrass | 100 | | 100 | | 100 | | 100 | |
| 40* | Corn | 100 | | 100 | | 100 | | 100 | |
| | Mustard | $95^a$ | | $0^b$ | | $0^b$ | | $0^b$ | |
| | Crabgrass | 100 | | 100 | | 100 | | 100 | |
| | Barnyard grass | 100 | | 100 | | $40^a$ | | $40^a$ | |
| | Cotton | 0 | | 0 | | 0 | | 0 | |
| 41 | Corn | 100 | | 100 | | 100 | | 100 | |
| (c isomer) | | $0^a$ | | $0^b$ | | $0^b$ | | $0^b$ | |
| | Crabgrass | 100 | | 100 | | 100 | | 100 | |
| | Barnyard grass | 100 | | 100 | | $80^a$ | | $90^a$ | |
| | Cotton | 0 | | 0 | | 0 | | 0 | |
| 42 | Corn | 100 | | 100 | | 100 | | 100 | |
| (c isomer) | Mustard | $30^a$ | | $0^b$ | | $0^b$ | | $0^b$ | |
| | Crabgrass | 100 | | 100 | | 100 | | 100 | |
| | Barnyard grass | 100 | | 100 | | 100 | | $60^a$ | |
| | Cotton | 0 | | 0 | | 0 | | 0 | |
| 42 | Corn | 0 | | 0 | | 0 | | 0 | |
| (t isomer) | Mustard | 0 | | 0 | | 0 | | 0 | |
| | Crabgrass | 0 | | 0 | | 0 | | 0 | |
| | Barnyard grass | 0 | | 0 | | 0 | | 0 | |
| | Cotton | 0 | | 0 | | 0 | | 0 | |
| 43 | Corn | 100 | | $70^a$ | | 100 | | $30^b$ | |
| (cis isomer) | Mustard | $0^b$ | | $0^b$ | | $0^b$ | | $0^b$ | |
| | Crabgrass | 100 | | 100 | | $90^a$ | | $80^a$ | |
| | Barnyard grass | 100 | | 100 | | $90^a$ | | $80^a$ | |
| | Cotton | $0^b$ | | $0^b$ | | $0^b$ | | 0 | |
| 44 | Corn | 100 | | 100 | | 100 | | 100 | |
| (cis isomer) | Mustard | $0^b$ | | $0^b$ | | $0^b$ | | 0 | |
| | Crabgrass | 100 | | 100 | | 100 | | 100 | |
| | Barnyard grass | 100 | | 100 | | 100 | | 100 | |
| | Cotton | 0 | 0 | | 0 | | 0 | | |
| 45 | Lima bean | 100 | | $0^b$ | | $0^b$ | | $0^b$ | |
| (c isomer) | Corn | 100 | | 100 | | 100 | | 100 | |
| | Lettuce | $0^b$ | | $0^b$ | | $0^b$ | | $0^b$ | |
| | Mustard | $0^b$ | | $0^b$ | | $0^b$ | | 0 | |
| | Crabgrass | 100 | | 100 | | 100 | | 100 | |
| 46 | Lima bean | $75^a$ | | $0^b$ | | $0^b$ | | $30^b$ | |
| (c isomer) | Corn | 100 | | 100 | | 100 | | 100 | |
| | Lettuce | $0^b$ | | $0^b$ | | $0^b$ | | $0^b$ | |
| | Mustard | $0^b$ | | $0^b$ | | $0^b$ | | 0 | |
| | Crabgrass | 100 | | 100 | | 100 | | 100 | |
| 47 | Lima bean | $50^a$ | | $0^b$ | | $0^b$ | | $0^b$ | |
| (c isomer) | Corn | 100 | | 100 | | 100 | | 100 | |
| | Lettuce | $0^b$ | | 0 | | 0 | | 0 | |
| | Mustard | $0^b$ | | $0^b$ | | $0^b$ | | 0 | |
| | Crabgrass | 100 | | 100 | | $90^a$ | | $50^b$ | |
| 48 | Lima bean | $0^b$ | | $0^b$ | | 0 | | 0 | |
| (c-isomer) | Corn | 100 | | 100 | | 100 | | 100 | |
| | Lettuce | $0^b$ | | $0^b$ | | $0^b$ | | $0^b$ | |
| | Mustard | 100 | | $0^b$ | | $0^b$ | | $0^b$ | |
| | Crabgrass | 100 | | 100 | | 100 | | 100 | |
| 49* | Corn | 100 | | $20^a$ | | $0^a$ | | $0^a$ | |
| | Mustard | 0 | | 0 | | 0 | | 0 | |
| | Crabgrass | 100 | | 100 | | $90^a$ | | $70^a$ | |
| | Barnyard grass | $90^a$ | | $70^a$ | | $50^a$ | | $50^a$ | |
| | Cotton | 0 | | 0 | | 0 | | 0 | |
| 50* | Corn | $60^a$ | | $40^a$ | | $0^a$ | | $0^a$ | |
| | Mustard | 0 | | 0 | | 0 | | 0 | |
| | Crabgrass | 100 | | $90^a$ | | $90^a$ | | $70^a$ | |
| | Barnyard grass | $50^a$ | | $30^a$ | | $20^a$ | | $20^a$ | |
| | Cotton | 0 | | 0 | | 0 | | 0 | |
| 51* | Corn | | | 0 | | 0 | | 0 | |
| | Mustard | | | 0 | | 0 | | 0 | |
| | Crabgrass | | | $70^b$ | | 30 | | 0 | |
| | Barnyard grass | | | $50^b$ | | 10 | | 0 | |
| | Cotton | | | 0 | | 0 | | 0 | |
| 52 | Lima bean | 100 | | $50^b$ | | $0^b$ | | $0^b$ | |
| (c-isomer) | Corn | 100 | | 100 | | 100 | | $70^b$ | |
| | Lettuce | $0^b$ | | $0^b$ | | $0^b$ | | $0^b$ | |
| | Mustard | $0^b$ | | $0^b$ | | $0^b$ | | $0^b$ | |
| | Crabgrass | 100 | | 100 | | 100 | | $70^a$ | |

Table 7-continued

Preemergence Herbicidal Activity of Substituted
5-Benzoyloxy-1,3-dioxanes (response at indicated rate)

| Compound of Example | Species | Rates in Pounds per Acre | | | | | | | |
|---|---|---|---|---|---|---|---|---|---|
| | | 8.0 | 6.0 | 4.0 | 3.0 | 2.0 | 1.5 | 1.0 | 0.75 |
| 53 (c-isomer) | Lima bean | $0^b$ | | 0 | | 0 | | 0 | |
| | Corn | 100 | | 100 | | 100 | | 100 | |
| | Lettuce | $0^b$ | | $0^b$ | | $0^b$ | | 0 | |
| | Mustard | $0^b$ | | $0^b$ | | $0^b$ | | 0 | |
| | Crabgrass | 100 | | 100 | | 100 | | 100 | |
| 54 (c-isomer) | Lima bean | $0^b$ | | $0^b$ | | 0 | | 0 | |
| | Corn | 100 | | 100 | | — | | 100 | |
| | Lettuce | $0^b$ | | $0^b$ | | $0^b$ | | 0 | |
| | Mustard | $0^b$ | | $0^b$ | | $0^b$ | | 0 | |
| | Crabgrass | 100 | | 100 | | 100 | | 100 | |
| 55 | Lima bean | | 0 | | 0 | | 0 | | 0 |
| | Corn | | 100 | | $0^b$ | | 0 | | 0 |
| | Mustard | | $0^b$ | | 0 | | 0 | | — |
| | Crabgrass | | 100 | | $80^a$ | | $80^a$ | | 100 |
| | Barnyard grass | | 100 | | $90^a$ | | $80^a$ | | $40^a$ |
| 56 | Corn | 100 | | 100 | | $80^a$ | | 100 | |
| | Mustard | 0 | | 0 | | 0 | | 0 | |
| | Crabgrass | 100 | | 100 | | 100 | | 100 | |
| | Barnyard grass | $80^a$ | | $50^a$ | | $20^a$ | | $10^a$ | |
| | Cotton | 0 | | 0 | | 0 | | $0^b$ | |
| 57 | Corn | 100 | | 100 | | $40^a$ | | 0 | |
| | Mustard | $0^b$ | | $0^b$ | | 0 | | 0 | |
| | Crabgrass | 100 | | 100 | | $90^a$ | | $90^a$ | |
| | Barnyard grass | 100 | | 100 | | $80^a$ | | $60^a$ | |
| | Cotton | 0 | | 0 | | 0 | | 0 | |
| 58 (c isomer) | Lima bean | $50^b$ | | $30^b$ | | 0 | | 0 | |
| | Corn | 100 | | 100 | | $70^a$ | | $70^a$ | |
| | Lettuce | $0^b$ | | $0^b$ | | 0 | | 0 | |
| | Mustard | $0^b$ | | $0^b$ | | $0^b$ | | 0 | |
| | Crabgrass | 100 | | 100 | | 100 | | 100 | |
| 59 | Lima bean | 0 | | 0 | | 0 | | 0 | |
| | Corn | 100 | | 100 | | 100 | | $70^a$ | |
| | Lettuce | 0 | | 0 | | 0 | | 0 | |
| | Mustard | $0^b$ | | $0^b$ | | $0^b$ | | 0 | |
| | Crabgrass | 100 | | 100 | | 100 | | 100 | |
| 60 | Lima bean | | 0 | | 0 | | 0 | | |
| | Corn | | $80^b$ | | 20 | | 0 | | |
| | Mustard | | 0 | | 0 | | 0 | | |
| | Lettuce | | 0 | | 0 | | 0 | | |
| | Crabgrass | | $60^b$ | | $40^b$ | | 0 | | |
| 61 (c isomer) | Lima bean | $0^b$ | | $0^b$ | | 0 | | 0 | |
| | Corn | 100 | | 100 | | $70^a$ | | 100 | |
| | Mustard | 0 | | 0 | | 0 | | 0 | |
| | Lettuce | $0^b$ | | $0^b$ | | $0^b$ | | 0 | |
| | Crabgrass | 100 | | 100 | | 100 | | 100 | |
| 62 (c isomer) | Lima bean | $0^b$ | | 0 | | 0 | | 0 | |
| | Corn | 100 | | 100 | | 100 | | 100 | |
| | Mustard | $0^b$ | | 0 | | 0 | | 0 | |
| | Lettuce | $0^b$ | | 0 | | 0 | | 0 | |
| | Crabgrass | 100 | | 100 | | 100 | | $70^b$ | |
| 63 | Lima bean | $0^b$ | | $0^b$ | | 0 | | 0 | |
| | Corn | 100 | | 100 | | 100 | | $30^b$ | |
| | Mustard | $0^b$ | | $0^b$ | | 0 | | 0 | |
| | Lettuce | $0^b$ | | $0^b$ | | 0 | | 0 | |
| | Crabgrass | 100 | | 100 | | 100 | | 100 | |
| 64 (c isomer) | Lima bean | 100 | | 100 | | $70^b$ | | 0 | |
| | Corn | 100 | | 100 | | 100 | | 100 | |
| | Mustard | $0^b$ | | $0^b$ | | $0^b$ | | $0^b$ | |
| | Lettuce | $0^b$ | | $0^b$ | | $0^b$ | | $0^b$ | |
| | Crabgrass | 100 | | 100 | | 100 | | 100 | |
| 65 (c isomer) | Lima bean | — | | 0 | | 0 | | 0 | |
| | Corn | 100 | | $30^a$ | | $0^b$ | | $0^b$ | |
| | Mustard | 0 | | 0 | | 0 | | 0 | |
| | Lettuce | $0^b$ | | $0^b$ | | 0 | | 0 | |
| | Crabgrass | 100 | | $30^a$ | | $20^a$ | | $20^b$ | |
| 66 (mixture) | Corn | $80^a$ | | $80^a$ | | $40^a$ | | $0^a$ | |
| | Mustard | $0^b$ | | $0^b$ | | 0 | | 0 | |
| | Crabgrass | 100 | | 100 | | 100 | | 100 | |
| | Barnyard grass | 100 | | 100 | | 100 | | $95^a$ | |
| | Cotton | 0 | | 0 | | 0 | | 0 | |
| 66 (c isomer) | Corn | 100 | | 100 | | 100 | | $20^a$ | |
| | Mustard | 0 | | 0 | | 0 | | 0 | |
| | Crabgrass | 100 | | 100 | | 100 | | 100 | |
| | Barnyard grass | $50^b$ | | $60^b$ | | $60^a$ | | $10^a$ | |
| | Cotton | 0 | | 0 | | 0 | | 0 | |
| 66 (t isomer) | Corn | 0 | | 0 | | 0 | | 0 | |
| | Mustard | 0 | | 0 | | 0 | | 0 | |
| | Crabgrass | 0 | | 0 | | 0 | | 0 | |
| | Barnyard grass | 0 | | 0 | | 0 | | 0 | |
| | Cotton | 0 | | 0 | | 0 | | 0 | |
| 67 (c isomer) | Lima bean | $75^{bc}$ | | $0^{bc}$ | | $0^{bc}$ | | $0^{bc}$ | |
| | Corn | 100 | | 100 | | 100 | | $70^a$ | |
| | Lettuce | $0^{bc}$ | | $0^{bc}$ | | $0^{bc}$ | | 0 | |
| | Mustard | $0^{bc}$ | | $0^{bc}$ | | $0^{bc}$ | | $0^{bc}$ | |
| | Crabgrass | 100 | | 100 | | 100 | | 100 | |
| 67 (t isomer) | Lima bean | $30^{bc}$ | | $0^{bc}$ | | $0^{bc}$ | | 0 | |
| | Corn | 100 | | 100 | | $30^a$ | $0^{bc}$ | | |
| | Lettuce | $0^{bc}$ | | 0 | | 0 | | 0 | |

Table 7-continued
Preemergence Herbicidal Activity of Substituted 5-Benzoyloxy-1,3-dioxanes (response at indicated rate)

| Compound of Example | Species | Rates in Pounds per Acre | | | | | | | |
|---|---|---|---|---|---|---|---|---|---|
| | | 8.0 | 6.0 | 4.0 | 3.0 | 2.0 | 1.5 | 1.0 | 0.75 |
| | Mustard | $0^{bc}$ | | $0^{bc}$ | | $0^{bc}$ | | 0 | |
| | Crabgrass | 100 | | $80^a$ | | $30^a$ | | $0^{bc}$ | |

[a]Surviving plants severely injured, probably will not survive
[b]Surviving plants injured, probably will survive
[c]Plants severely stunted
*Rate is that of cis-isomer applied
**Applied as produced without regard to cis-content For herbicidal applications, the active 1,3-dioxanes are formulated by admixture, in herbicidally effective amounts, with the adjuvants and carriers normally employed for facilitating the dispersion of active ingredients for agricultural applications, recognizing the fact that the formulation and mode of application of a toxicant may affect the activity of the material in a given application. Thus, these active herbicidal compounds may be formulated as granules of relatively large particle size, as wettable powders, as emulsifiable concentrates, as powdery dusts, as solutions, or as any of several other known types of formulations, depending on the desired mode of application. Preferred formulations or both pre- and post-emergence herbicidal applications are wettable powders, emulsifiable concentrates, and granules. These formulations may contain as little as 0.5% to as much as 95% or more by weight of active ingredient.

Wettable powders are in the form of finely divided particles which disperse readily in water or other dispersant. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5–95% of active ingredient by weight and usually also contain a small amount of wetting, dispersing or emulsifying agent to facilitate wetting and dispersion. For example, a useful wettable powder formulation contains 80.8 parts by weight of the active dioxane, 17.9 parts by weight of palmetto clay, and 1.0 part by weight of sodium lignosulfonate and 0.3 part by weight of sulfonated aliphatic polyester as wetting agents.

Emulsifiable concentrates are homogeneous liquid compositions which are dispersible in water or other liquid carrier, and may consist entirely of the active dioxane either with a liquid or solid emulsifying agent, or may also contain a liquid carrier, such as xylene, heavy aromatic naphthas, isophorone, and other nonvolatile organic solvents. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition. For example, a useful emulsifiable concentrate formulation contains 20.0 parts by weight of the active dioxane, 75 parts by weight of monochlorobenzene and 5.0 parts by weight of sulfated ethoxylated nonylphenol.

Granular formulations, wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5–25% of active ingredient and may also contain small amounts of other ingredients which may include surface-active agents such as wetting agents, dispersing agents or emulsifiers; oils such as heavy aromatic naphthas, kerosene or other petroleum fractions, or vegetable oils; and/or stickers such as dextrins, glue or synthetic resins. The average particle size of the granules is usually between 150 and 2400 microns. For example, a useful granular formulation contains 5.05 parts by weight of the active dioxane, 5.00 parts by weight of corn oil, and 89.95 parts by weight of crushed corn cobs.

Typical wetting, dispersing or emulsifying agents used in agricultural formulations include, for example, the alkyl and alkylaryl sulfonates and sulfates and their sodium salts; ethoxylated alcohols; ethoxylated alkylphenols; sulfonated oils; ethoxylated fatty amine salts; fatty acid esters of polyhydric alcohols; and other types of surface-active agents, many of which are available in commerce, including those of the anionic, nonionic, cationic and amphoteric types. The surface-active agent, when used, normally comprises from 1 to 15% by weight of the herbicidal composition.

Dusts, which are free-flowing admixtures of the active ingredient with finely divided solids such as talc, clays, flours and other organic and inorganic solids which act as dispersants and carriers for the toxicant, are useful formulations for soil-incorporated applications; the finely divided solids have an average particle size of less than about 50 microns.

Pastes, which are homogeneous suspension of a finely divided solid toxiant in a liquid carrier such as water or oil, are employed for specific purposes. These formulations normally contain about 5–95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene or other organic solvents. Pressurized sprays, typically aerosols wherein the active ingredient is dispersed in finely divided form as a result of vaporization of a low boiling dispersant solvent carrier, such as the Freons, may be used.

Typically herbicidal compositions in solid state (e.g. wettable powders, dusts, or granules) are packaged in paper (or plastic) bags containing, say, 2, 5, 10 or 15 pounds of the herbicidal composition and labelled with directions for the herbicidal use. Liquid herbicidal compositions (e.g. emulsifiable concentrates or pastes) are commonly packaged in quart or gallon rigid containers, e.g. jars or cans, similarly labelled. The herbicidal compositions of this invention may be packaged similarly.

It is understood that the foregoing detailed description is merely given by way of illustration and that many variations may be made therein without departing from the spirit of the invention.

We claim:

1. A herbicidally active compound of the formula

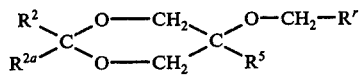

in which

R² is hydrogen or an alkyl, haloalkyl, cyanoalkyl, aryl, arylalkyl, aryloxyalkyl, cycloalkyl, arylalkoxyalkyl, alkoxyalkyl, alkenyl (including substituted alkenyl), alkynyl, alkylthioalkyl, alkylsulfinylalkyl or alkylsulfonylalkyl where any aryl radical is phenyl which is unsubstituted or carries a single "X" substituent as defined below;

R⁵ is hydrogen, alkyl, haloalkyl or cyanoalkyl;

Rʳ is monovalent aromatic phenyl which is unsubstituted or has one, two or three "Y" substituents as defined below:

R²ᵃ is hydrogen or alkyl; there being a cis relationship between the —OCH₂Rʳ group and any R² group except when R² and R²ᵃ both are hydrogen;

X is H, F, Cl, Br, lower alkyl, trifluoromethyl, lower alkoxy or benzyloxy;

Y is H, F, Cl, Br, CN, trifluoromethyl, lower alkyl or lower alkoxy;

said compound having at least one phenyl group having an X or Y substituent other than hydrogen.

2. Compounds as in claim 1 in which at least one of "X" or "Y" is other than hydrogen and is at an ortho-position of the "Y" carrying ring or is at a meta-position of the "X" carrying ring.

3. A compound as in claim 1 in which Rʳ is mono-ortho-substituted phenyl.

4. A compound of claim 1 which is cis-5-(2-fluorobenzyloxy)-2-phenyl-1,3-dioxane; cis-5-(2-methylbenzyloxy)-2-phenyl-1,3-dioxane; cis-5-benzyloxy-2-(3-chlorophenyl)-1,3-dioxane; cis-5-benzyloxy-2-(2-fluorophenyl)-1,3-dioxane, cis-5-(4-methylbenzyloxy)-2-phenyl-1,3-dioxane; cis-5-(2-bromobenzyloxy)-2-phenyl-1,3-dioxane; cis-5-(4-fluorobenzyloxy)-2-phenyl-1,3-dioxane; cis-5-(3-fluorobenzyloxy)-2-phenyl-1,3-dioxane; cis-5-(2,6-dichlorobenzyloxy)-2-phenyl-1,3-dioxane; cis-5-(2-chlorobenzyloxy)-2-phenyl-1,3-dioxane; cis-5-benzyloxy-2-(3-fluorophenyl)-1,3-dioxane; cis-5-(2-fluorobenzyloxy)-2-(3-fluorophenyl)-1,3-dioxane; cis-5-2-fluorobenzyloxy)-2-(3-methylphenyl)-1,3-dioxane; cis-5-(2-fluorobenzyloxy)-2-(3-chlorophenyl)-1,3-dioxane; cis-5-benzyloxy-2-(3-benzyloxyphenyl)-1,3-dioxane; cis-5-benzyloxy-2-(3-methoxyphenyl)-1,3-dioxane; cis-2-(3-chlorophenyl)-5-(2-methylbenzyloxy)-1,3-dioxane; r-2-chloromethyl-c-5-(2-fluorobenzyloxy)-5-methyl-1,3-dioxane; r-2-ethyl-c-5-(2-fluorobenzyloxy)-5-methyl-1,3-dioxane; r-2-ethyl-c-5-(2-methylbenzyloxy)-5-methyl-1,3-dioxane; or r-2-ethyl-5-methyl-c-5-(2-methylbenzyloxy)-1,3-dioxane.

5. A compound of claim 1 which is cis-5-(2-methylbenzyloxy)-2-phenyl-1,3-dioxane.

* * * * *